(12) United States Patent
Dhar et al.

(10) Patent No.: US 7,199,125 B2
(45) Date of Patent: Apr. 3, 2007

(54) SPIRO-CYCLIC COMPOUNDS USEFUL AS ANTI-INFLAMMATORY AGENTS

(75) Inventors: T. G. Murali Dhar, Newtown, PA (US); Edwin Iwanowicz, San Diego, CA (US); Michele Launay, Rueil Malmaison (FR); Dominique Potin, Epone (FR); Magali Jeannine Blandine Maillet, Suresnes (FR); Eric Nicolai, Rueil Malmaison (FR)

(73) Assignees: Bristol-Myers Squibb Company, Princeton, NJ (US); Cerep SA, Rueil-Malmaison, Cedex (FR)

( * ) Notice: Subject to any disclaimer, the term of this patent is extended or adjusted under 35 U.S.C. 154(b) by 242 days.

(21) Appl. No.: 10/957,255

(22) Filed: Oct. 1, 2004

(65) Prior Publication Data
US 2005/0119279 A1    Jun. 2, 2005

Related U.S. Application Data

(60) Provisional application No. 60/508,165, filed on Oct. 2, 2003.

(51) Int. Cl.
C07D 497/20 (2006.01)
C07D 498/20 (2006.01)
A61K 31/424 (2006.01)
A61K 31/429 (2006.01)
A61K 31/506 (2006.01)

(52) U.S. Cl. ............... 514/256; 514/365; 514/376; 544/335; 548/147; 548/216

(58) Field of Classification Search ............ 544/335; 548/147, 216; 514/256, 365, 376
See application file for complete search history.

(56) References Cited

U.S. PATENT DOCUMENTS

| 3,941,744 | A | 3/1976 | Murayama et al. | |
|---|---|---|---|---|
| 4,066,615 | A | 1/1978 | Murayama et al. | |
| 4,241,208 | A | 12/1980 | Murayama et al. | |
| 6,022,875 | A | 2/2000 | Zimmer et al. | |
| 6,710,064 | B2 * | 3/2004 | Launay et al. | 514/387 |
| 6,897,225 | B1 * | 5/2005 | Sircar et al. | 514/333 |
| 2002/0143035 | A1 | 10/2002 | Launay et al. | |
| 2003/0232817 | A1 * | 12/2003 | Fleck | 514/228.2 |
| 2006/0074099 | A1 * | 4/2006 | DelMonte et al. | 514/278 |
| 2006/0148836 | A1 * | 7/2006 | Dhar et al. | 514/278 |

FOREIGN PATENT DOCUMENTS

| JP | 2003-2834 | 1/2003 |
|---|---|---|
| WO | WO 98/39303 | 9/1998 |
| WO | WO 99/20617 | 4/1999 |
| WO | WO 99/20618 | 4/1999 |
| WO | WO 99/49856 | 10/1999 |
| WO | WO 01/06984 | 2/2001 |
| WO | WO 01/07044 | 2/2001 |
| WO | WO 01/07048 | 2/2001 |
| WO | WO 01/07052 | 2/2001 |
| WO | WO 01/07440 | 2/2001 |
| WO | WO 01/30781 | 5/2001 |
| WO | WO 01/45704 | 6/2001 |
| WO | WO 02/00653 | 1/2002 |
| WO | WO 02/44181 | 6/2002 |
| WO | WO 03/029245 | 4/2003 |
| WO | WO 03/053354 | 7/2003 |
| WO | WO 03/066636 | 8/2003 |

OTHER PUBLICATIONS

Anderson et al., Peptides, 24, 487-501, 2003.*
Dedrick et al., Expert Opin. Biol. Ther., 3(1), 85-95, 2003.*
Herold et al., Cellular Immiunology, 157(2), 489-500, Sep. 1994, Abstract.*
Kelly, The Journal of Immunology, 1999, 163, 5173-5177, 1999.*
Last-Barney et al., J. Am. Chem. Soc., 123, 5643-5650, 2001.*
Lavigne et al., Expert Opin. Biol. Ther., 5(3), 313-320, 2005.*
Liu et al., J. Med. Chem., 44, 1202-1210, 2001.*
Simmons, Current Opinion in Pharmacology, 5, 398-404, 2005.*
Moriyama et al., The Journal of Immunology, 157, 3737-3743, 1996.*
Noguera et al., Am. J. Respir. Crit. Care Med., 158, 1664-1668, 1998.*
Woska Jr. et al., Journal of Immunological Methods, 277, 101-115, 2003.*

(Continued)

Primary Examiner—Fiona T. Powers
(74) Attorney, Agent, or Firm—Laurelee A. Duncan

(57) ABSTRACT

The present invention is directed to compounds having the formula (I):

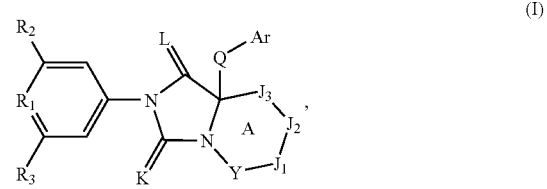

(I)

useful in treating inflammatory and immune diseases, in which K and L are independently, O or S; Q is —C(=O)— or optionally substituted $C_{1-6}$alkylene; Ar is optionally-substituted aryl or heteroaryl; $J_1$, $J_2$, $J_3$ and Y are selected so that ring A is a five-to-six membered optionally-substituted cycloalkenyl or heterocyclo ring having 0 to 2 nitrogen heteroatoms; $R_1$ is N or $C(R_9)$; and $R_2$ and $R_3$ are as defined in the specification.

18 Claims, No Drawings

OTHER PUBLICATIONS

Wu et al., J. Med. Chem., 47, 5356-5366, 2004.*
Yusuf-Makagiansar et al., Medicinal Research Reviews, 22(2), 146-167, 2002.*
Anderson, D.C. et al., "Leukocyte LFA-1, OKM1, p150,95 deficiency syndrome: functional and biosynthetic studies of three kindreds", Federation Proceedings, vol. 44, No. 10, pp. 2671-2677 (1985).
Brandstetter, T.W. et al., "Glucofuranose Analogues of Hydantocidin", Tetrahedron, vol. 52, No. 32, pp. 10721-10736 (1996).
Brandstetter, T.W. et al., "Spirohydantoins of Glucofuranose: Analogues of Hydantocidin", Tetrahedron Letters, vol. 36, No. 12, pp. 2149-2152 (1995).
Couture, P. et al., "Chemistry of cyclic aminooxycarbenes", Can. J. Chem., vol. 75, pp. 1281-1294 (1997).
Diamond, M.S. et al., "The dynamic regulation of integrin adhesiveness", Current Biology, vol. 4, No. 6, pp. 506-517 (1994).
Górski, A., "The role of cell adhesion molecules in immunopathology", Immunology Today, vol. 15, No. 6, pp. 251-255 (1994).
Park, K.-H. et al., "Preparation of a 900-Member Chemical Compound Library of Hydantoin- and Isoxazoline-Containing Heterocycles Using Multipin Technology", J. Comb. Chem., vol. 3, No. 2, pp. 171-176 (2001).
Sanfilippo, P.J. et al., "Novel Thiazole Based Heterocycles as Inhibitors of LFA-1/CAM-1 Mediated Cell Adhesion", J. Med. Chem., vol. 38, No. 7, pp. 1057-1059 (1995).

* cited by examiner

SPIRO-CYCLIC COMPOUNDS USEFUL AS ANTI-INFLAMMATORY AGENTS

This application claims the benefit of priority from U.S. Provisional Application Ser. No. 60/508,165 filed Oct. 2, 2003, the entirety of which is incorporated herein by reference.

FIELD OF THE INVENTION

The present invention relates to spiro-cyclic compounds, pharmaceutical compositions containing them, and methods of using such compounds in treating inflammatory or immune disease.

BACKGROUND OF THE INVENTION

Cells adhere to other cells and to substrates through specific, regulated processes that are critical to various biological functions. The proper functioning of the immune system is dependent upon adhesive interactions and cell migration. A key event in an immune response involves the migration of leukocytes to a disease site. During an inflammatory response, leukocytes are recruited to the site of injury and extravasated by a series of cellular interactions involving cell-cell and cell-substrate adhesion.

One family of molecules that serves an important adhesive function is integrins. Integrins are expressed on cell surfaces and function in cell-cell and cell-substrate adhesion. Integrins are alpha-beta heterodimers: each integrin has an alpha ($\alpha$) subunit non-covalently binded to a beta ($\beta$) subunit. When activated, integrins bind to extracellular ligands and induce adhesion (the expression of integrins on a cell surface alone is inadequate for adhesion—they must be activated to become adhesive). The integrin activation state is transient, such that there is a rapid flux between adhesive and non-adhesive states which is important for cell movement, e.g., a cell is endowed with the ability to rapidly adhere to various cell surfaces and matrices and to migrate among cells and tissue.

There are four known integrins having a $\beta_2$ or CD18 subunit which comprise the CD11/CD18 integrin sub-family, namely, Lymphocyte Function-associated Antigen 1 (LFA-1) (CD11a/CD18 or $\alpha_L\beta_2$); Macrophage Antigen 1 (Mac-1) (CD11b/CD18 or $\alpha_M\beta_2$); p150,95 (CD11c/CD18 or $\alpha_X\beta_2$); and $\alpha_D\beta_2$. The CD11/CD18 family of integrins is also referred to as Leukointegrins as they are expressed on the surface of various leukocyte cells, and they mediate a number of inflammation-related cellular interactions. See Diamond et al., "*The Dynamic Regulation of Integrin Adhesiveness,*" *Current Biology*, Vol. 4 (1994) at pp. 506–532.

Ligands to LFA-1 and Mac-1 comprise the intercellular adhesion molecule (ICAM) ICAM-1. The primary CD11/CD18 integrin is LFA-1, which also binds with ICAM-2 and ICAM-3. ICAMs are found on endothelium cells, leukocytes, and other cell types, and their interaction with CD11/CD18 integrins is critical to immune system function. The interaction between the CD18 integrins, particularly LFA-1, and ICAMs mediates antigen presentation, T-cell proliferation, and adhesion between the endothelium and activated leukocytes which is necessary for leukocytes to migrate from the circulatory system into tissue. A condition termed "Leukocyte Adhesion Deficiency" has been identified in patients having a deficiency in CD18 integrins. These patients are unable to mount a normal inflammatory or immune response; they suffer from disorders such as recurrent infections, poor wound healing, granulocytosis, progressive periodontitis, and umbilical cord separation. See Anderson et al., "*Leukocyte LFA-1, OKMI,* p150,95 *Deficiency Syndrome: Functional and Biosynthesis Studies of Three Kindreds,*" *Fed. Proc.*, Vol. 44 (1985), at pp. 2671–2677.

While sufficient levels of CD18 integrins interacting with ICAMs are needed to mount a normal immune response, significant cellular and tissue injury can result in chronic inflammatory states where there is an inappropriate influx of leukocytes to the disease site. Continuous recruitment of leukocytes from blood vessels into inflamed tissue, as in chronic inflammatory states, can perpetuate tissue injury and lead to excessive fibrous repair and autoimmune disease. Thus, inhibition of the interaction between LFA-1 and/or Mac-1 and their ICAMs can be advantageous in treating inflammatory or immune disease. For example, monoclonal antibody blockade of either ICAM or LFA-1 has been shown to prevent the migration of leukocytes into tissue and the subsequent development of inflammatory disease in animal models of rheumatoid arthritis, inflammatory bowel disease, and pulmonary inflammation (e.g., asthma). Knockout mice deficient in ICAMs have reduced susceptibility to induced arthritis, ischemia injury, impaired lung inflammatory responses, and increased tolerance to transplantations (e.g. heart grafts). See Anderson, supra. Antibodies blocking the ICAM-LFA-1 interaction reportedly suppress cardiac allograft rejection and islet cell xenograft rejection in animal models. See Gorski, "*The Role of Cell Adhesion Molecules in Immunopathology,*" *Immunology Today*, Vol. 15 (1994), at pp. 251–255.

Compounds inhibiting CD18 integrins, ICAMs, and/or the LFA-1:ICAM interaction could potentially demonstrate a wide range of utilities in treating inflammatory or immune diseases. Blocking LFA-1 reportedly inhibits the influx of leukocytes in almost every system, including the skin, peritoneum, synovium, lung, kidney, and heart, and blocking ICAM-1 would be expected to have similar effects. Also, present therapies for many inflammatory and immune diseases have drawbacks. For example, current treatments for asthma include $\beta_2$-agonists, inhaled corticosteroids, and $LTD_4$ antagonists. However, $\beta_2$-agonists have limited efficacy and inhaled corticosteroids raise safety concerns. To treat psoriasis, current therapies include PUVA, methotrexate, cyclosporin A, and topical treatments. The first three of these therapies raise toxicity issues over long-term (6–9 month) use, whereas topical treatments have limited efficacy. Additionally, these treatments typically are applied only in response to flares and not as a prophylaxis measure.

Compounds that reportedly inhibit LFA-1/ICAM for use as anti-inflammatory agents include thiadiazole-based compounds (see Intern. Pub. No. WO 99/20,618, "*Thiadiazole Amides Useful as Anti-Inflammatory Agents*" filed by Pharmacia & Upjohn Co.; and WO 99/20,617, also to Pharmacia and Upjohn); and thiazole compounds linked to phenyl and pyrazole rings (Sanfilippo et al., "*Novel Thiazole Based Heterocyclos as Inhibitors of LFA-1/ICAM-Mediated Cell Adhesion,*" *J. Med. Chem.*, Vol. 38 (1995) at pp. 1057–1059). Small molecules that reportedly are antagonists to the binding of ICAMs with CD18 integrins include various benzylamines and 2-bromobenzoyltryptophan compounds (see Intern. Pub. No. WO99/49,856, "*Antagonists for Treatment of CD11/CD18 Adhesion Receptor Mediated Disorders,*" filed by Genentech, Inc.), and 1-(3,5 dichlorophenyl) imidazolidines (see Intern. Pub. No. WO98/39303, "*Small Molecules Useful in the Treatment of Inflammatory Disease,*" filed by Boehringer Ingelheim Pharmaceuticals, Inc. See also Boehringer patent applications WO 01/07052, WO 01/07048, WO 01/07044, WO 01/06984, and WO 01/07440). Hydantoin compounds are disclosed in WO 01/30781 A2 (published May 3, 2001) to Tanabe Seiyaku Co. Ltd, WO 03029245 A1 (published Apr. 10, 2003) to Bristol-Myers Squibb; and WO 01030781 A1 (published May 3, 2003) to Bristol-Myers Squibb.

As may be appreciated, those in the field of pharmaceutical research continue to seek to develop new compounds and compositions for treating inflammatory and immune disease such as inhibitors of Leukointegrins and/or ICAMs. Particularly in the area of immune response, many individuals respond differently to different drugs. Thus, there is an interest in providing consumers not only with pharmaceutical compositions demonstrating increased effectiveness and reduced side-effects but also different structures or mechanisms of action to provide consumers with a choice of options. Diazaspiroheptane compounds are disclosed in Park et al., "*Preparation of a 990 Member Chemical Compound Library of Hydantoin and Isoxazoline-Containing Heterocyclos Using Multipin Technology,*" *J. Comb. Chem.*, Vol. 3(2) (2001), at pp. 171–76. Spiro heterocyclos are also disclosed in Couture et al., "*Chemistry of Cyclic Aminooxycarbenes,*" *Can. J. Chem.*, Vol. 75(9) (1997) at pp. 1281–1294; Brandstetter et al., "*Glucofuranose Analogs of Hydanocidin,*" *Tetrahedron*, Vol. 52(32) (1996), at pp. 10721–10736; Brandstetter et al., "*Spirohydantois of Glucofuranose: Analogs of Hydantocidin,*" *Tetrahedron Lett.*, Vol. 36(12) (1995) at pp. 2149–52; in U.S. Pat. Nos. 6,022,875, 4,241,208, 4,066,615, and 3,941,744, and International patent application WO 01/45704.

Each of the patents, patent applications and publications referenced above and hereinafter is incorporated herein by reference.

SUMMARY OF THE INVENTION

The present invention provides compounds useful in treating inflammatory or immune disease having the formula (I):

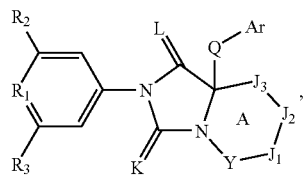

its stereoisomers, or a pharmaceutically-acceptable salt, hydrate, or prodrug thereof, in which:
K and L are independently O or S;
Q is a bond, —C(=O)— or branched or straight chain $C_{1-6}$alkylene optionally substituted with one to two $R_4$;
Ar is aryl or heteroaryl;
Y is a bond or —C($R_{6a}R_{7a}$)—;
$J_1$ is —N($R_5$)— or —C($R_{6b}R_{7b}$)—;
$J_2$ is —N($R_5$)— or —C($R_{6c}R_{7c}$)—;
$J_3$ is N($R_5$) or C($R_{7d}R_{7d}$);
provided that only one of $J_1$, $J_2$ and $J_3$ may be —N($R_5$)—, so that ring A is a five-to-six membered cycloalkyl or heterocyclo ring having from 0 to 2 heteroatoms;
$R_1$ is N or C($R_9$);
$R_2$ and $R_3$ are independently selected from hydrogen, halogen, nitro, cyano, alkyl, substituted alkyl, alkenyl, substituted alkenyl, —$SR_{12}$, —$OR_{12}$, —$NR_{12}R_{13}$, —$CO_2R_{12}$, —C(=O)$R_{12}$, —C(=O)$NR_{12}R_{13}$, aryl, heterocyclo, cycloalkyl, and heteroaryl;

$R_4$ is selected from OH, O($C_{1-6}$alkyl), halogen, cyano, $CF_3$, $OCF_3$, $NH_2$, NH(6alkyl), and N($C_{1-6}$alkyl)$_2$;

$R_5$ is selected from hydrogen, alkyl, substituted alkyl, alkenyl, substituted alkenyl, —$NR_{14}R_{15}$, —C(=O)$R_{14}$, —$CO_2R_{14}$, —C(=O)$NR_{14}R_{15}$, —S(O)$_pR_{15a}$, —$SO_2NR_{14}R_{15}$, aryl, heterocyclo, cycloalkyl, and heteroaryl; or when $R_5$ is joined to atom $J_1$, $J_2$ or $J_3$, $R_5$ may be taken together with one of $R_{6a}$, $R_{6b}$ $R_{6c}$ or $R_{6d}$ attached to an adjacent atom of ring A to form a fused heterocyclo or heteroaryl ring;

at least one of $R_{6a}$ with $R_{7a}$, or $R_{6b}$ with $R_{7b}$, or $R_{6c}$ with $R_{7c}$ are taken together to form a spiro-cycloalkyl or spiro-heterocyclo ring; provided that the spiro-heterocyclo ring is not $C_{2-3}$ alkylenedioxy;

$R_{6a}$, $R_{6b}$, $R_{6c}$, $R_{6d}$, $R_{7a}$, $R_{7b}$, $R_{7c}$, and $R_{7d}$ which do not form a spiro-cycloalkyl or spiro-heterocyclo ring are independently selected from hydrogen, halogen, alkyl, substituted alkyl, alkenyl, substituted alkenyl, nitro, cyano, —$SR_{16}$, —$OR_{16}$, —$NR_{16}R_{17}$, —C(=O)$R_{16}$, —$CO_2R_{16}$, —C(=O)$NR_{16}R_{17}$, —$NR_{16}$C(=O)$R_{17}$, —$NR_{16}$C(=O)$OR_{17}$, —S(O)$_qR_{17a}$, —$NR_{16}SO_2R_{17a}$, —$SO_2NR_{16}R_{17}$, aryl, heterocyclo, cycloalkyl, and heteroaryl;

or $R_{6a}$, $R_{6b}$, $R_{6c}$, $R_{6d}$, $R_{7a}$, $R_{7b}$, $R_{7c}$, and $R_{7d}$ which do not form a spiro-cycloalkyl or spiro-heterocyclo ring and which are attached to the same carbon atom may be taken together to form a keto group;

or $R_{6a}$, $R_{6b}$, $R_{6c}$, $R_{6d}$, $R_{7a}$, $R_{7b}$, $R_{7c}$, and $R_{7d}$ which do not form a spiro-cycloalkyl or spiro-heterocyclo ring and which are attached to adjacent carbon atoms may be taken together to form a fused benzo, cycloalkyl, heterocyclo, or heteroaryl ring;

$R_9$ is selected from hydrogen, halogen, nitro, cyano, alkyl, substituted alkyl, alkenyl, substituted alkenyl, —$SR_{18}$, —$OR_{18}$, —$NR_{18}R_{19}$, —$CO_2R_{18}$, —C(=O)$R_{18}$, —C(=O)$NR_{18}R_{19}$, aryl, heterocyclo, cycloalkyl, and heteroaryl;

$R_{12}$, $R_{13}$, $R_{14}$, $R_{15}$, $R_{16}$, $R_{17}$, $R_{18}$, and $R_{19}$ (i) are selected independently of each other from hydrogen, alkyl, substituted alkyl, cycloalkyl, aryl, heteroaryl, and heterocyclo; or (ii) any two of $R_{12}$, $R_{13}$, $R_{14}$, $R_{15}$, $R_{16}$, $R_{17}$, $R_{18}$, and $R_{19}$ when attached to the same nitrogen atom (as in $NR_{12}R_{13}$, $NR_{14}R_{15}$, $NR_{16}R_{17}$, or $NR_{18}R_{19}$) may be taken together to form a heteroaryl or heterocyclo ring, with the remainder of $R_{10}$, $R_{11}$, $R_{12}$, $R_{13}$, $R_{14}$, $R_{15}$, $R_{16}$, $R_{17}$, $R_{18}$, and $R_{19}$ being selected independently from hydrogen, alkyl, substituted alkyl, cycloalkyl, aryl, heteroaryl, and heterocyclo;

$R_{15a}$, and $R_{17a}$ are independently selected from alkyl, substituted alkyl, cycloalkyl, aryl, heteroaryl, and heterocyclo;

p is 1, 2, or 3; and q is 1, 2, or 3.

The present invention is also directed to pharmaceutical compositions useful in treating immune or inflammatory diseases comprising compounds of formula (I), or stereoisomers, pharmaceutically-acceptable salts, pharmaceutically-acceptable carriers or diluents thereof. The invention further relates to methods of treating immune or inflammatory diseases comprising administering to a patient in need of such treatment a therapeutically-effective amount of a compound according to formula (I).

DETAILED DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$C_1$–$C_6$ alkyl" refers to a straight or branched chain alkane (hydrocarbon) radical containing from 1 to 6 carbon atoms, such as methyl, ethyl, propyl, isopropyl, n-butyl, t-butyl, and isobutyl.

"Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single or multiple halo substitutents) trifluoromethyl, trifluoromethoxy, cyano, nitro, alkyl, cycloalkyl, alkenyl, cycloalkenyl, alkynyl, heterocyclo, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocyclo, or aryl; $R_b$, $R_c$ and $R_d$ are independently hydrogen, alkyl, cycloalkyl, heterocyclo, aryl, or heteroaryl, or said $R_b$ and $R_c$ together with the N to which they are bonded optionally form a heterocyclo; and $R_e$ is alkyl, cycloalkyl, alkenyl, alkynyl, heterocyclo, aryl or heteroaryl. Exemplary substituents also include spiro-attached or fused cylic substituents, especially spiro-attached cycloalkyl, spiro-attached heterocyclo, fused cycloalkyl, fused heterocyclo, fused aryl, or fused heteroaryl, In both the aforementioned groups of exemplary substitutents, groups such as alkyl, cycloalkyl, alkenyl, alkynyl, cycloalkenyl, heterocyclo, aryl and heteroaryl can themselves be optionally substituted, as described infra.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "cycloalkyl" refers to fully saturated and partially unsaturated hydrocarbon rings of 3 to 9, preferably 3 to 7 carbon atoms. The term "cycloalkyl" includes such rings Exemplary such groups include cyclopropyl, cyclobutyl, cyclopentyl, cyclohexyl, cycloheptyl, cyclobutenyl, cyclopentenyl, cyclohexenyl, etc. Cycloalkyl groups may be unsubstituted or substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached heterocyclo, fused cycloalkyl, fused cycloalkenyl, fused heterocyclo, fused aryl, or fused heteroaryl, the aforementioned cycloalkyl, heterocyclo, aryl and heteroaryl can themselves be optionally substituted.

The term "aryl" refers to unsubstituted or substituted cyclic, aromatic hydrocarbon groups which have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). The aryl group may be substituted by one or more substituents, preferably 1 to 3 substituents, at any point of attachment. Exemplary substituents include, but are not limited to, nitro, cycloalkyl, cyano, alkyl or substituted alkyl, as well as those groups recited above as exemplary alkyl substituents. Exemplary substituents also include fused cylic, especially fused cycloalkyl, fused heterocyclo, fused aryl, or fused heteroaryl.

The term "heterocyclo" refers non-aromatic 3 to 7 membered monocyclic groups, 7 to 11 membered bicyclic groups, and 10 to 15 membered tricyclic groups, in which at least one of the rings has at least one heteroatom (O, S or N). Each heerocyclo group may be unsubstituted or substituted. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom in any fashion, including spiro-attachments. The heterocyclo group may be substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, as well as those groups recited above as exemplary alkyl substituents. Exemplary substituents also include spiro-attached or fused cylic substituents at any available point or points of attachment, especially spiro-attached cycloalkyl, spiro-attached cycloalkenyl, spiro-attached heterocyclo, fused cycloalkyl, fused cycloalkenyl, fused heterocyclo, fused aryl, or fused heteroaryl, the aforementioned cycloalkyl, cycloalkenyl, heterocyclo, aryl and heteroaryl can themselves be optionally substituted.

Exemplary monocyclic heterocyclo groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. "Substituted heteroaryl" refers to heteroaryl groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, cyano, alkyl or substituted alkyl, as well as those groups recited above as exemplary alkyl substituents. Exemplary substituents also include or fused cylic substituents at any available points of attachment, especially fused cycloalkyl, fused cycloalkenyl, fused heterocyclo, fused aryl and fused heteroaryl, the aforementioned cycloalkyl, cycloalkenyl, heterocyclo, aryl and heteroaryl can themselves be optionally substituted.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0–2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

When a functional group is termed "protected", this means that the group is chemically modified to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1999).

Unless otherwise indicated, any heteroatom with unsatisfied valences is assumed to have hydrogen atoms sufficient to satisfy the valences.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms (i.e. "stereoisomers"), are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings.

Throughout the specifications, groups and substituents thereof may be chosen to provide stable moieties and compounds.

Preferred Compounds

Preferred compounds of the invention include compounds of formula (I) in which one or more, preferably all, of the following substituents are as defined below:
K and L are both O;
Q is a straight chain $C_{1-6}$alkylene (preferably methylene);
Ar is phenyl optionally substituted one to three $R_{20}$;

$R_2$ and $R_3$ are selected from halogen, $(C_{1-6})$alkyl, cyano, halo$(C_{1-6})$alkyl, halo$(C_{1-6})$alkoxy, nitro, phenyloxy, benzyloxy, and phenylthio;

$R_{20}$ at each occurrence is independently selected from halogen, $C_{1-6}$alkyl, hydroxy, $(C_{1-6})$alkoxy, halo$(C_{1-6})$alkyl, halo$(C_{1-6})$alkoxy, cyano, nitro, —$CO_2H$, —C(=O)H, —$CO_2(C_{1-6})$alkyl, —C(=O) $(C_{1-6})$alkyl, —C(=O)NH $(CH_2)_rCO_2H$, —C(=O)NH$(CH_2)_rCO_2(C_{1-6}$alkyl), and $S(O)_2(C_{1-6}$alkyl); or from phenyl, benzyl, phenyloxy, benzyloxy and heteroaryl in turn optionally substituted with one to two of halogen, $(C_{1-6})$alkyl, hydroxy, $(C_{1-6})$alkoxy, halo$(C_{1-6})$alkyl, halo$(C_{1-6})$alkoxy, cyano, nitro, —$CO_2H$, —C(=O)H, —$CO_2(C_{1-6})$alkyl, and/or —C(=O) $(C_{1-6})$alkyl; or alternatively, two $R_{20}$ groups join together with each other to form a fused benzo ring; and r is 1, 2, 3, or 4.

Particularly preferred compounds, or a pharmaceutically-acceptable salt, hydrate, prodrug, or stereoisomer thereof, within the scope of formula (I) are those wherein Q-Ar together form:

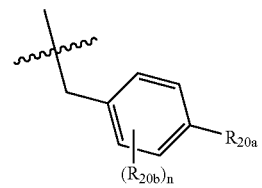

wherein $R_{20a}$ and $R_{20b}$ are independently selected from halogen, $C_{1-6}$alkyl, hydroxy, $(C_{1-6})$alkoxy, halo$(C_{1-6})$alkyl, halo $(C_{1-6})$alkoxy, cyano, nitro, —$CO_2H$, —C(=O)H, —$CO_2$ $(C_{1-6})$alkyl, —C(=O) $(C_{1-6})$alkyl, —C(=O)NH$(CH_2)_r$ $CO_2H$, —C(=O)NH$(CH_2)_rCO_2(C_{1-6}$alkyl), and $S(O)_2$ $(C_{1-6}$alkyl); or from phenyl, benzyl, phenyloxy, benzyloxy and heteroaryl in turn optionally substituted with one to two of halogen, $C_{1-6}$alkyl, hydroxy, $(C_{1-6})$alkoxy, halo $(C_{1-6})$alkyl, halo$(C_{1-6})$alkoxy, cyano, nitro, —$NH_2$, —NH $(C_{1-6}$alkyl), —N$(C_{1-6}$alkyl$)_2$, —$CO_2H$, —C(=O)H, —$CO_2(C_{1-6})$alkyl, and/or —C(=O) $(C_{1-6})$alkyl; or alternatively, two $R_{20b}$ groups join together with each other or one $R_{20b}$ joins together with $R_{20a}$ to form a fused benzo ring;

n is 0, 1, or 2; and r is 1, 2, 3, or 4.

Other particularly preferred compounds, or a pharmaceutically-acceptable salt, hydrate, prodrug, or stereoisomer thereof, within the scope of formula (I) are those wherein one or more, preferably all, of the following substituents are defined as below:

Y is a bond;

$J_1$ is —$CHR_{6b}$—;

$J_2$ is —$C(R_{6c}R_{7c})$— wherein $R_{6c}$ with $R_{7c}$ are taken together to form a spirocycloalkyl or spiroheterocyclo ring;

$J_3$ is $CH(R_{6d})$;

$R_1$ is $C(R_8)$ (preferably CH);

$R_2$ and $R_3$ are independently halogen.

$R_{6b}$, and $R_{6d}$ are independently selected from a) hydrogen, halogen, and cyano;

b) —SR$_{16}$, —OR$_{16}$, —NR$_{16}$R$_{17}$, —C(=O)R$_{16}$, —CO$_2$R$_{16}$, —C(=O)NR$_{16}$R$_{17}$, —NR$_{16}$C(=O)R$_{17}$, —NR$_{16}$C(=O)OR$_{17}$, —S(O)$_q$R$_{17a}$, —NR$_{16}$SO$_2$R$_{17a}$, and —SO$_2$NR$_{16}$R$_{17}$; and c) (C$_{1-6}$)alkyl, phenyl, four to seven membered heterocyclo, C$_{3-7}$cycloalkyl, and five to six membered heteroaryl, each of which in turn is optionally substituted with one to two groups selected from R$_{22}$;

R$_{16}$ and R$_{17}$ are selected independently from hydrogen, C$_{1-6}$alkyl, phenyl, four to seven membered heterocyclo, C$_{3-7}$cycloalkyl, and five to six membered heteroaryl, each of which in turn is optionally substituted with one to two groups selected from R$_{23}$;

R$_{17a}$ is C$_{1-6}$alkyl, phenyl, four to seven membered heterocyclo, C$_{3-7}$cycloalkyl, five to six membered heteroaryl each of which is optionally substituted with one to two groups selected from R$_{23}$; and R$_{22}$ and R$_{23}$ are at each occurrence selected independently from halogen, cyano, C$_{1-6}$alkyl, hydroxy, trifluoromethyl, trifluoromethoxy, —O(C$_{1-6}$alkyl), —C(=O)H, —C(=O)(C$_{1-6}$alkyl), —CO$_2$H, —CO$_2$(C$_{1-6}$alkyl), —C(=O)NH$_2$, —C(=O)NH$_2$, —C(=O)NH(C$_{1-6}$alkyl), —C(=O)N(C$_{1-6}$alkyl)$_2$, —NH$_2$, —NH(C$_{1-6}$alkyl), —N(C$_{1-6}$alkyl)$_2$, hydroxy(C$_{1-6}$)alkyl, methoxy(C$_{1-6}$)alkyl, ethoxy(C$_{1-6}$)alkyl, amino(C$_{1-6}$)alkyl, and halo(C$_{1-6}$)alkyl.

Alternatively, preferred compounds of the invention include compounds of formula (Ia)

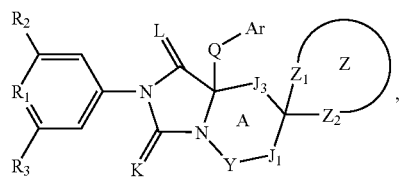

(Ia)

or a pharmaceutically-acceptable salt, hydrate, prodrug, or stereoisomer thereof, in which K and L are independently O or S;

Q is a bond, —C(=O)— or branched or straight chain C$_{1-6}$alkylene optionally substituted with one to two R$_4$ (Q is preferably C$_{1-6}$alkylene, especially methylene);

Ar is aryl or heteroaryl;

Y is a bond or —C(R$_{6a}$R$_{7a}$)—;

J$_1$ is —N(R$_5$)— or —C(R$_{6b}$R$_{7b}$)—;

J$_3$ is —N(R$_5$)— or —C(R$_{6d}$R$_{7d}$)—; provided, that only one of J$_1$ and J$_3$ may be —N(R$_5$)—, so that ring A is a five-to-six membered cycloalkyl or heterocyclo ring having from 0 to 2 heteroatoms;

Z$_1$ and Z$_2$ are independently NR$_{25}$, S or O; so that Z forms a spiro heterocyclic ring provided that Z is not a C$_{2-3}$ alkylenedioxy ring and that only one of Z$_1$ and Z$_2$ may be NR$_{25}$;

R$_1$ is N or C(R$_9$);

R$_2$ and R$_3$ are independently selected from hydrogen, halogen, nitro, cyano, alkyl, substituted alkyl, alkenyl, substituted alkenyl, —SR$_{12}$, —OR$_{12}$, —NR$_{12}$R$_{13}$, —CO$_2$R$_{12}$, —C(=O)R$_{12}$, —C(=O)NR$_{12}$R$_{13}$, aryl, heterocyclo, cycloalkyl, and heteroaryl;

R$_4$ is selected from OH, O(C$_{1-6}$alkyl), halogen, cyano, CF$_3$, OCF$_3$, NH$_2$, NH(C$_{1-6}$alkyl), and N(C$_{1-6}$alkyl)$_2$;

R$_5$ is selected from hydrogen, alkyl, substituted alkyl, alkenyl, substituted alkenyl, —NR$_{14}$R$_{15}$, —C(=O)R$_{14}$, —CO$_2$R$_{14}$, —C(=O)NR$_{14}$R$_{15}$, —S(O)$_p$R$_{15a}$, —SO$_2$NR$_{14}$R$_{15}$, aryl, heterocyclo, cycloalkyl, and heteroaryl; or when R$_5$ is joined to atom J$_1$, J$_3$ or Y, R$_5$ may be taken together with one of R$_{6a}$, R$_{6b}$ or R$_{6d}$ attached to an adjacent atom of ring A to form a fused heterocyclo or heteroaryl ring;

R$_{6a}$, R$_{6b}$, R$_{6d}$, R$_{7a}$, R$_{7b}$, R$_{7b}$ and R$_{7d}$ are independently selected from hydrogen, halogen, alkyl, substituted alkyl, alkenyl, substituted alkenyl, nitro, cyano, —SR$_{16}$, —OR$_{16}$, —NR$_{16}$R$_{17}$, —C(=O)R$_{16}$, —CO$_2$R$_{16}$, —C(=O)NR$_{16}$R$_{17}$, —NR$_{16}$C(=O)R$_{17}$, —NR$_{16}$C(=O)OR$_{17}$, —S(O)$_q$R$_{17a}$, —NR$_{16}$SO$_2$R$_{17a}$, —SO$_2$NR$_{16}$R$_{17}$, aryl, heterocyclo, cycloalkyl, and heteroaryl;

R$_9$ is selected from hydrogen, halogen, nitro, cyano, alkyl, substituted alkyl, alkenyl, substituted alkenyl, —SR$_{18}$, —OR$_{18}$, —NR$_{18}$R$_{19}$, —CO$_2$R$_{18}$, —C(=O)R$_{18}$, —C(=O)NR$_{18}$R$_{19}$, aryl, heterocyclo, cycloalkyl, and heteroaryl;

R$_{12}$, R$_{13}$, R$_{14}$, R$_{15}$, R$_{16}$, R$_{17}$, R$_{18}$, and R$_{19}$ (i) are selected independently of each other from hydrogen, alkyl, substituted alkyl, cycloalkyl, aryl, heteroaryl, and heterocyclo; or (ii) any two of R$_{12}$, R$_{13}$, R$_{14}$, R$_{15}$, R$_{16}$, R$_{17}$, R$_{18}$, and R$_{19}$ when attached to the same nitrogen atom (as in NR$_{12}$R$_{13}$, NR$_{14}$R$_{15}$, NR$_{16}$R$_{17}$, or NR$_{18}$R$_{19}$) may be taken together to form a heteroaryl or heterocyclo ring, with the remainder of R$_{12}$, R$_{13}$, R$_{14}$, R$_{15}$, R$_{16}$, R$_{17}$, R$_{18}$, and R$_{19}$ being selected independently from hydrogen, alkyl, substituted alkyl, cycloalkyl, aryl, heteroaryl, and heterocyclo;

R$_{11a}$, R$_{15a}$, and R$_{17a}$ are independently selected from alkyl, substituted alkyl, cycloalkyl, aryl, heteroaryl, and heterocyclo;

R$_{25}$ is selected from hydrogen, alkyl, substituted alkyl, alkenyl, substituted alkenyl, —NR$_{26}$R$_{27}$, —C(=O)R$_{26}$, —CO$_2$R$_{26}$, —C(=O)NR$_{26}$R$_{27}$, —S(O)$_p$R$_{27}$, —SO$_2$NR$_{26}$R$_{27}$, aryl, heterocyclo, cycloalkyl, and heteroaryl;

R$_{26}$, and R$_{27}$ are selected independently of each other front hydrogen, alkyl, substituted alkyl, cycloalkyl, aryl, heteroaryl, and heterocyclo;

p is 0, 1, 2, or 3; and q is 1, 2, or 3.

Particularly preferred compounds within the scope of formula (Ia), or a pharmaceutically-acceptable salt, hydrate, prodrug, or stereoisomer thereof, are those in which one or more, preferably all, of the following substituents re as defined below:

Y is a bond; and

Q-Ar together form:

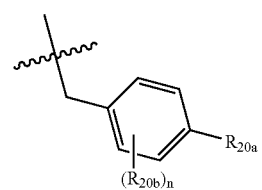

wherein

R$_1$ is CH.

R$_2$ and R$_3$ are independently halogen;

J$_1$ is —C(R$_{6b}$R$_{7b}$)—;

J$_3$ is —C(R$_{6b}$R$_{7b}$)—;

one of Z$_1$ or Z$_2$ is NR$_{25}$;

R$_{20a}$ and R$_{20b}$ are independently selected from halogen, C$_{1-6}$alkyl, hydroxy, (C$_{1-6}$)alkoxy, halo(C$_{1-6}$)alkyl, halo ($C_{1-6}$)alkoxy, cyano, nitro, —$CO_2H$, —C(=O)H, —$CO_2$($C_{1-6}$)alkyl, —C(=O) ($C_{1-6}$)alkyl, —C(=O)NH($CH_2$)$_r$$CO_2H$, —C(=O)NH($CH_2$)$_r$$CO_2$($C_{1-6}$alkyl), and S(O)$_2$($C_{1-6}$alkyl); or from phenyl, benzyl, phenyloxy, benzyloxy and heteroaryl in turn optionally substituted with one to two of halogen, $C_{1-6}$alkyl, hydroxy, ($C_{1-6}$)alkoxy, halo($C_{1-6}$)alkyl, halo($C_{1-6}$)alkoxy, cyano, nitro, —$NH_2$, —NH($C_{1-6}$alkyl), —N($C_{1-6}$alkyl)$_2$, —$CO_2H$, —C(=O)H, —$CO_2$($C_{1-6}$)alkyl, and/or —C(=O) ($C_{1-6}$)alkyl; or alternatively, two $R_{20b}$ groups join together with each other or one $R_{20b}$ joins together with $R_{20a}$ to form a fused benzo ring;

n is 0, 1, or 2; and r is 1, 2, 3, or 4.

Alternatively, preferred compounds of the invention include compounds of formula (Ib)

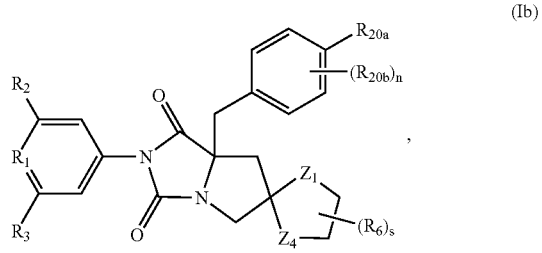

(Ib)

its stereoisomers, or a pharmaceutically-acceptable salt, hydrate, solvate, or prodrug thereof, in which:

one of $Z_1$ or $Z_2$ is $NR_{25}$ and the other of $Z_1$ or $Z_2$ is O or S;

$R_1$ is N or C($R_9$);

$R_2$ and $R_3$ are independently selected from halogen, ($C_{1-6}$) alkyl, cyano, halo($C_{1-6}$)alkyl, halo($C_{1-6}$)alkoxy, nitro, phenyloxy, benzyloxy, and phenylthio;

$R_6$ is selected from (a) halogen, nitro, and cyano; or from (b) —$SR_{16}$, —$OR_{16}$, —$NR_{16}R_{17}$, —C(=O)$R_{16}$, —$CO_2R_{16}$, —C(=O)$NR_{16}R_{17}$, —$NR_{16}C$(=O)$R_{17}$, —$NR_{16}C$(=O)$OR_{17}$, —S(O)$_q$$R_{17a}$, —$NR_{16}SO_2R_{17a}$, and —$SO_2NR_{16}R_{17}$; or from (c) alkyl, alkenyl, aryl, heterocyclo, cycloalkyl, and heteroaryl, in turn optionally substituted with one to two groups selected from $R_{22}$; and/or (d) two $R_6$ groups taken together form keto (=O), with the remainder of the $R_6$ groups selected from (a), (b), and (c);

$R_{16}$ and $R_{17}$ are selected independently of each other from hydrogen, $C_{1-6}$alkyl, phenyl, four to seven membered heterocyclo, $C_{3-7}$cycloalkyl, and five to six membered heteroaryl, each of which in turn is optionally substituted with one to two groups selected from $R_{23}$;

$R_{17a}$ is $C_{1-6}$alkyl, phenyl, four to seven membered heterocyclo, $C_{3-7}$cycloalkyl, five to six membered heteroaryl each of which is optionally substituted with one to two groups selected from $R_{23}$;

$R_{20a}$ and $R_{20b}$ are independently selected from halogen, $C_{1-6}$alkyl, hydroxy, ($C_{1-6}$)alkoxy, halo($C_{1-6}$)alkyl, halo ($C_{1-6}$)alkoxy, cyano, nitro, —$CO_2H$, —C(=O)H, —$CO_2$($C_{1-6}$)alkyl, —C(=O) ($C_{1-6}$)alkyl, —C(=O)NH($CH_2$)$_r$$CO_2H$, —C(=O)NH($CH_2$)$_r$$CO_2$($C_{1-6}$alkyl), and S(O)$_2$($C_{1-6}$alkyl); or from phenyl, benzyl, phenyloxy, benzyloxy and heteroaryl in turn optionally substituted with one to two of halogen, $C_{1-6}$alkyl, hydroxy, ($C_{1-6}$)alkoxy, halo ($C_{1-6}$)alkyl, halo($C_{1-6}$)alkoxy, cyano, nitro, —$NH_2$, —NH($C_{1-6}$alkyl), —N($C_{1-6}$alkyl)$_2$, —$CO_2H$, —C(=O)H, —$CO_2$($C_{1-6}$)alkyl, and/or —C(=O) ($C_{1-6}$) alkyl; or alternatively, two $R_{20b}$ groups join together with each other or one $R_{20b}$ joins together with $R_{20a}$ to form a fused benzo ring;

$R_{22}$, $R_{23}$ and $R_{24}$ are at each occurrence selected independently from halogen, cyano, nitro, $C_{1-6}$alkyl, hydroxy, trifluoromethyl, trifluoromethoxy, —O($C_{1-6}$alkyl), —C(=O)H, —C(=O)($C_{1-6}$alkyl), —$CO_2H$, —$CO_2$($C_{1-6}$alkyl), —C(=O)$NH_2$, —C(=O)$NH_2$, —C(=O)NH($C_{1-6}$alkyl), —C(=O)N($C_{1-6}$alkyl)$_2$, —$NH_2$, —NH($C_{1-6}$alkyl), —N($C_{1-6}$alkyl)$_2$, hydroxy($C_{1-6}$)alkyl, methoxy ($C_{1-6}$)alkyl, ethoxy($C_{1-6}$)alkyl, amino($C_{1-6}$)alkyl, and halo($C_{1-6}$)alkyl;

$R_{25}$ is selected from hydrogen, alkyl, substituted alkyl, alkenyl, substituted alkenyl, —$NR_{26}R_{27}$, —C(=O)$R_{26}$, —$CO_2R_{26}$, —C(=O)$NR_{26}R_{27}$, —S(O)$_p$$R_{27}$, —$SO_2NR_{26}R_{27}$, aryl, heterocyclo, cycloalkyl, and heteroaryl;

$R_{26}$ and $R_{27}$ are selected independently of each other from hydrogen, alkyl, substituted alkyl, cycloalkyl, aryl, heteroaryl, and heterocyclo n, s and and p are independently 0, 1, or 2;

q is 1, 2, or 3; and r is 0, 1, 2, 3 or 4.

Particularly preferred compounds within the scope of formula (Ib), or a pharmaceutically-acceptable salt, hydrate, prodrug, or stereoisomer thereof, are those in which one or more, preferably all, of the following substituents are as defined below:

$R_1$ is CH;

$R_2$ and $R_3$ are independently halogen;

$R_6$ is hydrogen, $C_{1-6}$alkyl, substituted $C_{1-6}$alkyl, —C(=O)$R_{26}$ or $CO_2R_{26}$;

$R_{20a}$ is cyano, halogen, aryl, or heteroaryl.

$R_{25}$ is hydrogen, $C_{1-6}$alkyl, substituted $C_{1-6}$alkyl, or —C(=O)$R_{26}$; and n is 0.

Especially preferred compounds are those having the formula, (i) (2R,5S,7a'S)-7a'-[(4-bromophenyl)-methyl]-2'-(3,5-dichlorophenyl)-5-methyldihydro-1'H,4H-spiro[1,3-oxazolidine-2,6'-pyrrolo[1,2-c]imidazole]-1',3',4(2'H)-trione;

(2R,5R,7a'S)-7a'-[(4-bromophenyl)-methyl]-2'-(3,5-dichlorophenyl)-5-methyldihydro-1'H,4H-spiro[1,3-oxazolidine-2,6'-pyrrolo[1,2-c]imidazole]-1',3',4(2'H)-trione;

(2R,5R,7a'S)-7a'-[(4-Bromophenyl)methyl]-2'-(3,5-dichlorophenyl)dihydro-5-methylspiro[oxazolidine-2,6'(5'H)-[1H]pyrrolo[1,2-c]imidazole]-1',3',4(2'H)-trione;

(2S,5R,7a'S)-7a'-[(4-Bromophenyl)methyl]-2'-(3,5-dichlorophenyl)dihydro-5-methylspiro[oxazolidine-2,6'(5'H)-[1H]pyrrolo[1,2-c]imidazole]-1',3',4(2'H)-trione;

(2R,7a'S)-7a'-[(4-Bromophenyl)methyl]-2'-(3,5-dichlorophenyl)dihydrospiro[oxazolidine-2,6'(5'H)-[1H]pyrrolo[1,2-c]imidazole]-1',3',4(2'H)-trione;

(2S,7a'S)-7a'-[(4-Bromophenyl)methyl]-2'-(3,5-dichlorophenyl)dihydrospiro[oxazolidine-2,6'(5'H)-[1H]pyrrolo[1,2-c]imidazole]-1',3',4(2'H)-trione;

4-[[(2R,5R,7a'S)-2'-(3,5-Dichlorophenyl)dihydro-5-methyl-1',3',4-trioxospiro[oxazolidine-2,6'(5'H)-[1H]pyrrolo[1,2-c]imidazol]-7a'(7'H)-yl]methyl]benzonitrile;

4-[[(2S,5R,7a'S)-2'-(3,5-Dichlorophenyl)dihydro-5-methyl-1',3',4-trioxospiro[oxazolidine-2,6'(5'H)-[1H]pyrrolo[1,2-c]imidazol]-7a'(7'H)-yl]methyl]-benzonitrile;

(2R,5R,7a'S)-2'-(3,5-dichlorophenyl)-7a'-[[4-(pyrimidin-4-yl)-phenyl)-methyl]-5-methyldihydro-1'H,4H-spiro[1,3-oxazolidine-2,6'-pyrrolo[1,2-c]imidazole]-1',3',4(2'H)-trione;

ethyl (4'S,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate;

ethyl (4'S,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate;

ethyl (4'R,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate;

ethyl (4'R,6S,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate;

(±) ethyl (4'S,7aS)-3'-acetyl-7a-ethyl-2-methyl-1,3-dioxotetrahydro-1H-spiro[pyrrolo[1,2-c]imidazole-6,2'-[1,3]thiazolidine]-4'-carboxylate;

(±) ethyl (4'S,7aS)-7a-(4-bromophenyl)-2-(3,5-dichlorophenyl)-1,3-dioxotetrahydro-1H-spiro[pyrrolo[1,2-c]imidazole-6,2'-[1,3]thiazolidine]-4'-carboxylate; or (ii) a pharmaceutically-acceptable salt, hydrate, prodrug, or stereoisomer thereof.

Methods of Preparation

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. The symbols used in the followoing schemes are defined as above, unless otherwise indicated.

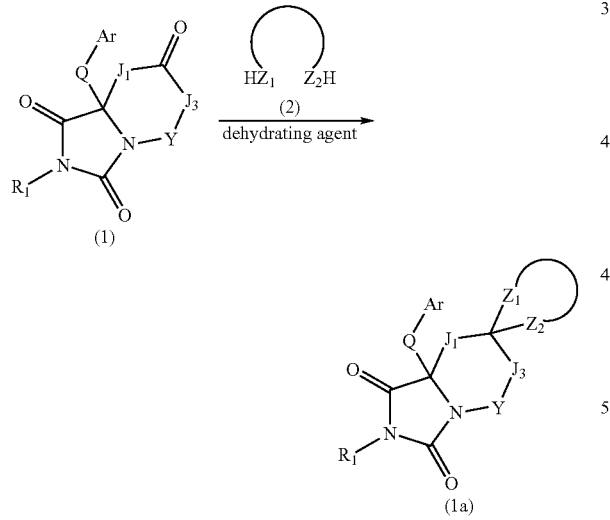

Compounds of the general formula (Ia) may be obtained from compounds of formula (1) by dehydrative cyclization. The choice of the dehydrating agent will be readily apparent to one skilled in the art of organic chemistry. Such methods are, for example described by Greene, Theodora W. and Wuts, Peter G. M. in "Protective groups in organic synthesis" 3$^{rd}$ Ed., (1999) Publisher (John Wiley and Sons, Inc., New York, N.Y). For example, if the reagent (2) is an amino-alcohol ($Z_1H=NH_2$, $Z_2H=OH$), compounds of formula (Ia) may be obtained by refluxing (1) and (2) in a solvent such as xylene, a catalytic amount of acid such a para-toluenesulfonic acid and at a temperature range of 100–140° C. with the azeotropic removal of water. Furthermore, if the reagent is an amino-thiol ($Z_1H=NH_2$, $Z_2H=SH$), compounds of formula (Ia) may be obtained for example by stirring (1) and (2) in a solvent such as ethanol at a temperature range of 20–50° C. (Refouvelet, Bernard et al.: Chem. Pharm. Bull., 1994, 42 (5), 1076–1083)

Compounds of the general formula (1) may be obtained by the oxidation of compounds of general formula (3) as shown in Scheme 2.

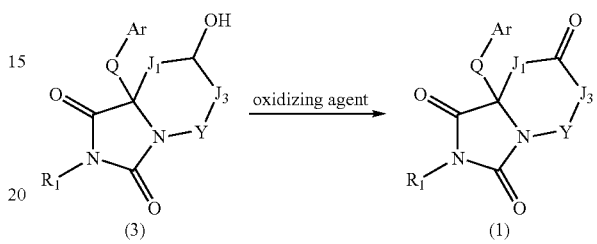

The choice of the oxidizing agent will be readily apparent to one skilled in the art of organic chemistry. Such methods are, for example described by Hudlicky, M., in "oxidations in organic chemistry", ACS monograph 186 (1990), American Chemical Society, Washington, D.C. For example, compounds of formula (1) may be obtained from compounds of formula (3) by using an oxidizing agent such as pyridinium chlorochromate, in a solvent like dichloromethane at temperatures ranging from 0° C. to 40° C.

Compounds of general formula (3) may be obtained by the protocol outlined in Scheme 3.

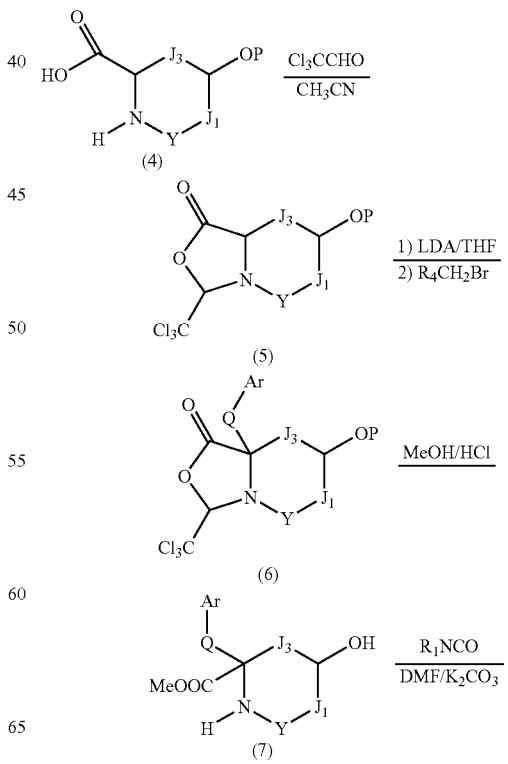

-continued

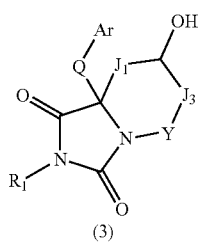

(3)

Compounds of formula (3) can be prepared by reacting the proline derivative (7) with an isocyanate ($R_1$NCO) in DMF in the presence of $K_2CO_3$. See Issartel et al., *Eur. J. Med. Chem. Chim. Ther.*, Vol. 31; 9 (1996), at pp. 717–724, incorporated herein by reference. The isocyantes useful for the preparation of compounds to this invention may be commercially available or readily prepared by many methods known to one skilled in the art of organic chemistry.

Compounds of formula (7) can be prepared by heating the oxazolidinone of formula (6) in refluxing methanolic HCl. See Remuzon et al., *J. Med. Chem.*, Vol. 35(15) (1992) p. 2898, incorporated herein by reference.

Compounds of formula (6) can be prepared from compounds of formula (5) by alkylating without loss of the optical activity the oxazolidinone of formula (5) with $BrCH_2$—Y in the presence of LDA in THF. See Wang et al., *Synlett*, Vol. 1 (1999), pp. 33–36, incorporated herein by reference.

Compounds of formula (5) can be prepared from compounds of formula (4) by cyclizing the proline compound of formula (4) with anhydrous chloral in acetonitrile. See Orsini et al., *J. Heterocyclic Chem.*, (1989), pp. 837–841, incorporated herein by reference.

Compounds of formula (4) can be obtained from commercially available sources or can readily be prepared by one skilled in the field.

Compounds of formula (X) can be obtained in a similar way as described above in Scheme 3 from 7 by replacing the isocyanate in Scheme 3 with an isothiocyanate (Scheme 4). Compounds of formula (X) can be processed as outlined in Schemes 1 and 2 above to give the thiohydantoin analog of compound 1a Scheme 4

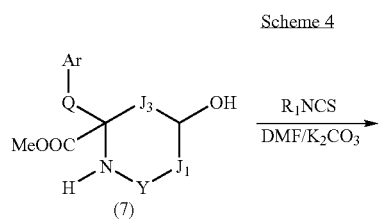

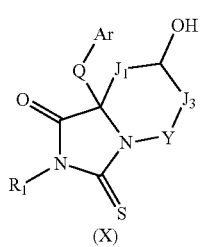

(X)

Alternatively compounds of formula (3) may be prepared by the sequence outlined in Scheme 5.

Scheme 5

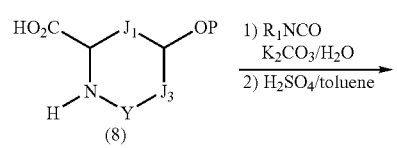

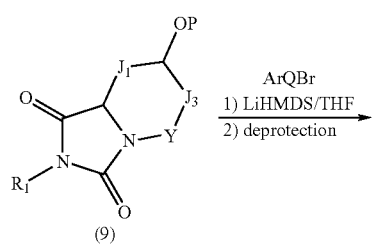

(9)

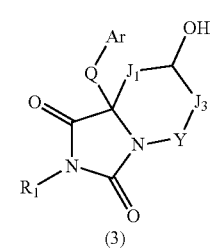

(3)

Compounds of formula (3) can be prepared from compounds of formula (9) by reacting (9) with $BrCH_2$—$R_4$ in the presence of LiHMDS or LDA and THF. See Kobayashi et al., *Bull. Chem. Soc. Jpn.*, Vol. 67; 11 (1994), at pp. 3082–3087, incorporated herein by reference. The protecting group on the oxygen can then be deprotected by one skilled in the art of organic chemistry. Such methods are, for example described by Greene, Theodora W. and Wuts, Peter G. M. in "Protective groups in organic synthesis" $3^{rd}$ Ed., (1999) Publisher (John Wiley and Sons, Inc., New York, N.Y).

Compounds of formula (9) can be prepared from compounds of formula (8) by reacting proline derivatives (8) with isocyanate $R^2$NCO in an aqueous basic media, then cyclizing the intermediate ureidoacid in refluxing toluene in the presence of a catalytic amount of sulfuric acid. See French patent No. FR230083 and Great Britain Pat. No. B1 503 244, titled "1,5-Alkylene-3-aryl Hydantoin Derivatives," both to Mitsubishi Chemical Indus., Inc., incorporated herein.

Compounds of formula (8) can be obtained from commercially available sources or can readily be prepared by one skilled in the field.

Compounds of formula (Y) can be obtained from (9) by reaction with either Lawesson's reagent or phosphorus pentasulfide (Scheme 6). Compounds of formula (X) can be processed as outlined in Schemes 1 and 2 above to give the dithiohydantoin analog of compound 1a Scheme 6

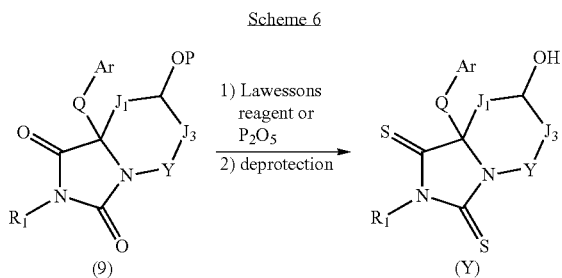

Utility

The compounds and compositions of this invention are antagonists of LFA-1, Mac-1, and/or ICAMs. Thus, they are useful in treating various inflammatory diseases and disorders associated with the action of LFA-1, Mac-1, and/or ICAMs, particularly LFA-1:ICAM-1. The term "Leukointegrin/ICAM-associated condition" is used herein for ease of reference to refer to those diseases or disorders that are associated with the action or levels of LFA-1, Mac-1 and/or ICAM-1, ICAM-2, or ICAM-3. As used herein the term "treating" includes prophylactic and therapeutic uses and refers to the alleviation of symptoms of a particular disorder in a patient, the improvement of an ascertainable measurement associated with a particular disorder, or the prevention of a particular immune response (such as transplant rejection). The term "patient" refers to a mammal, preferably a human.

The inventive compounds and compositions are useful for treating a wide range of conditions, as the action of LFA-1 and/or ICAMs is associated with the influx of leukocytes in almost every system, including the skin, peritoneum, synovium, lung, kidney and heart. The inventive compounds may be used to treat conditions resulting from a response of the specific immune system in a patient or the nonspecific immune system. Such conditions include, for example, graft vs host reactions and transplant rejection (e.g., kidney, liver, heart, lung, pancreas, bone marrow, cornea, small bowel, skin allografts, skin homografts and heterografts, etc.); psoriasis, organ-tissue autoimmune diseases (e.g., Raynaud's syndrome), autoimmune thyroiditis, dermatitis, multiple sclerosis, rheumatoid arthritis, insulin dependent diabetes mellitus, uveitis, inflammatory bowel disease including Crohn's disease and ulcerative colitis and systemic lupus erythematosus, adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infraction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome, pulmonary fibrosis, atherosclerosis, meningitis, encephalitis, experimental autoimmune encephalomyelitis, Sjorgen's syndrome, and juvenile onset diabetes. The compounds of the present invention also may be used to treat allergic conditions such as eczema and asthma or as an adjunct to minimize toxicity with cytokine therapy in the treatment of cancers. In view of their inhibition activity, the compounds may be used to treat inflammatory conditions that involve the infiltration of T-cells and chronic inflammatory responses, hypersensitivity reactions, such as skin hypersensitivity reactions (including poison ivy and poison oak), immune responses associated with delayed hypersensitivity mediated by cytokines and T-lymphocytes, and metastases.

The compounds of this invention further have utility in treating hypogonadism, frailty, osteoporosis, sexual dysfunction, wasting, such as wasting syndromes associated with cancer and AIDS, and anemia. The compounds further have utility in treating cancers, including but not limited to cancers of the breast, brain, skin, ovary, endometrium, bladder, prostate, lung, colon, lymphatic system, liver and kidney. The inventive compounds are useful for conditions such as hirsutism, Alzheimer's disease, non-insulin dependent diabetes mellitus, acne, seborrhea, alopecia, fibroids, hyperpilosity, cachexia, polycystic ovarian syndrome, anorexia, contraception, drug withdrawal syndrome, pregnancy termination, and benign prostate hypertrophy. The compounds are further useful as antiangiogenic agents. Additionally, the compounds may be useful as inhibitors of protein prenyltransferases, particularly farnesyltransferase and the prenylation of the oncogene protein Ras. As such, the inventive compounds may potentially be useful for treating and/or preventing the diseases and disorders referred to in WO 01/45704, which is incorporated herein by reference.

When used as anti-inflammatory agents, the compounds may be administered prior to the onset of, at, or after the initiation of inflammation. When used prophylactically, the compounds are preferably provided in advance of any inflammatory response or symptom (for example, prior to, at, or shortly after the time of an organ or tissue transplant but in advance of any symptoms or organ rejection). Administration of the compounds may prevent or attenuate inflammatory responses or symptoms.

The present invention thus provides methods for treating such conditions as those listed above, comprising administering to a subject in need thereof an effective amount of at least one compound of formula (I) or a salt thereof. Other therapeutic agents such as those described below may be employed in combination with the compounds of formula (I). In the methods of the present invention, such other therapeutic agent(s) may be administered prior to, simultaneously with, or following the administration of the inventive compounds.

The present invention also provides pharmaceutical compositions capable of treating the Leukointegrin/ICAM-associated conditions and above-described diseases and disorders. The inventive compositions may contain other therapeutic agents and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular, or intrastemal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a patient of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and the particular condition sought to be treated and its severity. Preferred subjects for treatment include animals, most preferably mammalian species such as humans, and domestic animals such as dogs, cats, horses, and the like, subject to Leukointegrin/ICAM associated conditions and/or subject to any of the above-referenced diseases and disorders.

The inventive compounds and compositions may be employed alone or in combination with each other and/or other suitable therapeutic agents useful in treating Leukointegrin/ICAM-associated conditions and diseases and disorders referenced above. Exemplary of such other therapeutic agents include corticosteroids, cyclosporin, methotrexate; CELLCEPT™ (mycophenolate mofetil), co-stimulation blockades, growth hormones, and growth hormone secretagogues. Additionally, the inventive compounds may be administered either alone or in combination with anti-cancer and cytotoxic agents and treatments useful in treating cancer or other proliferative diseases, for example, where the second drug has the same or different mechanism of action than the present compounds. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; famesyl-protein transferase inhibitors; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A–F and their analogs; plant-derived products, such as vinca alkaloids and epipodophyllotoxins; topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may be used in conjunction with radiation therapy.

Representative examples of these classes of anti-cancer and cytotoxic agents that may be used in combination with the inventive compounds include but are not limited to paclitaxel, cisplatin, carboplatin, doxorubicin, carmninomycin, daunorubicin, idarubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine, mechlorethamine hydrochloride, cyclophosphamhide, chlorambucil, ifosfamide, busulfan, carmustin, lomustine, semustine, streptozocin, thiotepa, dacarbazine, methotrexate, thioguanine, fludarabine, pentastatin, cladribin, cytarabine, bleomycin, mitomycin C, actinomycin D, safracins, saframycins, quinocarcins, discodermolides, vinorelbine, tamoxifen, estramustine, flutamide, buserelin, leuprolide, pteridines, diynes, levamisole, aflacon, interferon, interleukins, aldesleukin, filgrastim, sargramostim, rituximab, BCG, tretinoin, irinotecan, betamethasone, altretamine, and topotecan and any analogs or derivatives thereof.

Examples of anticancer and other cytotoxic agents that may be used in combination with the inventive compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416; and prenyl-protein transferase inhibitors as found in WO 97/30992 and WO 98/54966.

The above other therapeutic agents, when employed in combination with the compounds of the present invention, may be used, for example, in those amounts indicated in the Physicians' Desk Reference (PDR) or as otherwise determined by one of ordinary skill in the art.

The inventive compounds have been tested in cell-cell assays and demonstrated activity consistent with inhibition of LFA-1 and/or ICAM-1.

Assays

H1-HeLa Adhesion Assay

H1-Hela cells were released from their growth flask using versene (Gibco, Grand Island, N.Y.). Following centrifugation, the cells were resuspended in growth medium: DMEM (Gibco), 10% fetal calf serum (Hyclone, Logan, Utah), 1% Pen-Strep (Gibco), and 1% L-glutamine (Gibco) and plated for growth at 5,000 cells/well in a 96-well plate.

The next day, HSB-2 cells were divided to $2\times10^5$/ml in growth medium: RPMI 1640 (Gibco), 10% FCS, 1% Pen-Strep, and 1% L-glutamine. The next day (day #3), the cells were centrifuged at 534×G for 8 minutes, washed, and resuspended in HBSS at $5\times10_7$/ml. Calcein-AM, 10 µM (Molecular Probes, Eugene, Oreg.) and 100 nM phorbol myristate acetate (SIGMA, St. Louis, Mo.) were added to the labeling and activation mix. Following incubation at 37° C. for 30 minutes, ten ml of HBSS was added and the cells centrifuged as above. The cell pellet was then resuspended and counted.

While the HSB-2 cells were labeling, the medium was aspirated from the H1-HeLa cells and the plates washed once with HBSS, followed by the addition of 50 µl of HBSS. An additional 50 µl of HBSS containing compound solution, DMSO, or anti-CD18 antibody was then added to each well. To the H1-HeLa cells were added 200,000 HSB-2 cells/well in 100 µl, followed by incubation in the dark for 30 minutes. The wells were then washed three times to remove the unbound cells. A fluorescence plate reader was then used to determine the number of bound HSB-2 cells. The percent inhibition due to the compound was calculated using the vehicle control as 0% inhibition and the antibody blocked adhesion as 100% inhibition.

HUVEC Adhesion Assay

On day 1, human umbilical vein endothelial cells (HUVEC) (passage 3, Clonetics, San Diego, Calif.) were placed into a T-75 flask containing EGM bulletkit media (Clonetics) for growth.

When the HUVEC were 90% confluent (typically day 4), 96-well tissue culture plates were coated with 100 µl/well of 2.5 µg/ml mouse Type IV collagen (Gibco) diluted in 0.1 M acetic acid. Following incubation for at least three hours, the collagen was removed and the plate washed three times with HBSS (Gibco). The HUVEC flask was trypsinized, and HUVEC were plated on the collagen coated wells at 1250 cells/200 µl/well for use four days later. Twenty hours prior to use, the medium was removed and cells were stimulated with 200 µl of 1 µg/ml lipopolysaccharide (LPS, Sigma, St. Louis, Mo.) in EGM. When the cells were 90% confluent (typically day 8), the LPS-containing medium was removed, the wells were washed with HBSS, and 50 µl of HBSS was added to the wells. An additional 50 µl containing compound solution, DMSO or blocking anti-CD18 was then added to each well.

On day 7, HSB-2 cells were then divided to $2\times10^5$/ml in RPMI 1640 (Gibco), 10% FCS (Hyclone, Logan, Utah), 1% Pen-Strep (Gibco), and 1% L-glutarmne (Gibco). The following day, the cells were centrifuged at 534×G for 8 minutes, washed, and resuspended in HBSS at $5\times10_7$/ml. For activation and labeling, calcein-AM, 10 µM (Molecular Probes, Eugene, Oreg.) and 100 nM phorbol myristate acetate (Sigma, St. Louis, Mo.) were added and the cells incubated at 37° C. for 30 minutes. Following the addition of ten ml of HBSS, the cells were centrifuged, resuspended, and counted.

To the HUVEC cells were added 200,000 labeled and activated HSB-2 cells/well in 100 µl, followed by incubation in the dark for 30 minutes. To remove unbound cells, the wells were washed three times with HBSS. A fluorescence plate reader was used to determine the number of HSB-2 cells bound. The percent inhibition due to the compound was calculated with the vehicle control set at 0% inhibition and the antibody-blocked adhesion set at 100% inhibition.

EXAMPLES

The following Examples illustrate embodiments of the inventive compounds and starting materials, and are not intended to limit the scope of the claims. For ease of reference, the following abbreviations are used herein:

Abbreviations
$AlCl_3$=aluminum chloride
$Ac_2O$=acetic anhydride
AcONa=sodium acetate
Bn=benzyl
Bu=butyl
t-Bu=tertiary butyl
Boc=tert-butyl oxycarbonyl
bp=boiling point
$CDCl_3$=deutered chloroform
$CH_3CN$=acetonitrile
DCM=dichloromethane
DMAP=4-dimethylaminopyridine
DCC=dicyclohexylcarbodiimide
DIPEA or DIEA=N,N-diisopropylethylamine
DME=1,2-dimethoxyethane
DMF=dimethyl formamide
EDCI=1-3-dimethylaminopropyl)-3-ethylcarbodiimide
$Et_2O$=diethyl ether HOBT=1-hydroxybenzotriazole
eq=equivalent(s)
h or hr=hour(s)
EtOAc=ethyl acetate
g=gram(s)
h or hr=hour(s)
HCl=hydrochloric acid
HPLC=high performance liquid chromatography
KOH=potassium hydroxide
$K_2CO_3$=potassium carbonate
l=liter
$LiAlH_4$=lithium aluminum hydride
LDA=lithium diisopropyl amide
MeCN=acetonitrile
MeOH=methanol
mg(s)=milligram(s)
$MgSO_4$=magnesium sulfate
NaH=sodium hydride
$NaHCO_3$=sodium bicarbonate
$Na_2SO_4$=sodium sulfate
NaOH=sodium hydroxide
NMP=1-methyl-2-pyrrolidinone
pet. ether=petroleum ether
$PBr_3$=phosphorus tribromide
$(Ph_3P)_4Pd$=tetrakis(triphenylphosphine)palladium(0)
PS=polystyrene
$SiO_2$=silica
$SOCl_2$=thionyl chloride
TEA (or $Et_3N$)=triethylamine
THF=tetrahydrofuran
TFA=trifluoro acid acid
mg=milligram(s)
ml=milliliter
μl=microliter
mmol=millimole
μmol=micromole
mol=mole
mp=melting point
RT=room temperature
sat or sat'd=saturated Preparations

Preparation 1

(3R,6R,7aS)-6-tert-butoxy-3-(trichloromethyl)tetrahydro-1H-pyrrolo[1,2-c][1,3]oxazol-1-one

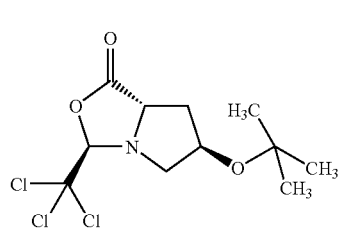

To a suspension of trans-3-t-butoxy-L-proline (1 g) (0.53 mmol) in 20 mL of acetonitrile was added anhydrous chloral 0.5 mL (1 eq.), and the mixture was allowed to stir at RT for 72 h. The remaining starting material was removed by filtration and the acetonitrile evaporated. The resulting white solid residue was stirred with isopropyl ether, filtered, and washed with pentane to afford the above titled compound (1.45 g). Mp=147° C. $^1$H NMR ($CDCl_3$): 5.1 (1H,s), 4.20 (1H,dd), 4.10 (1H,dd), 3.13–3.32 (2H,m), 2.05–2.25 (2H, m), 1.20 (9H,s).

Preparation 2

(3R,6R,7aS)-6-tert-butoxy-7a-(4-Bromo-benzyl)-3-(trichloromethyl)tetrahydro-1H-pyrrolo[1,2-c][1,3]oxazol-1-one

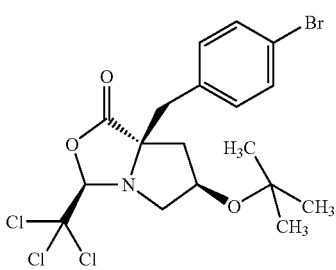

To a suspension of (3R,6R,7aS)-6-tert-butoxy-3-(trichloromethyl)tetrahydro-1H-pyrrolo[1,2-c][1,3]oxazol-1-one (1.45 g) (Prep. 1) in 10 mL of dry THF at −78° C. was added 6.9 mL of a 1M solution of LDA in THF (1.5 eq). The reaction mixture was stirred for 1 h, and a solution of 4-bromobenzyl bromide (3.5 g) (3 eq.) in 5 mL of THF was added. The reaction mixture was stirred for an additional hour at −70° C., allowed to warm to −20° C., then partitioned between EtOAc and water. The aqueous layer was extracted with another volume of EtOAc. The combined organic extracts were dried over $MgSO_4$, filtered and evaporated under reduced pressure to afford a brown oil which was purified by $SiO_2$ chromatography (eluent: pet. ether then pet. ether/DCM-50/50) to give the above-titled compound as a white solid (0.8 g). Mp=140° C. $^1$H NMR ($CDCl_3$): 7.45 (2H,d), 7.25 (2H,d), 5.0 (1H,s), 3.95 (1H,m), 3.25 (1H,d), 3.10 (1H,dd), 2.95 (1H,d), 2.50 (1H,dd), 2.30 (1H,dd), 1.85 (1H,dd), 1.13 (9H,s).

Preparation 3 methyl (4R)-2-(4-bromobenzyl)-4-hydroxy-L-prolinate

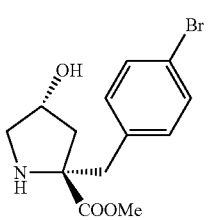

To a suspension of (3R,6R,7aS)-6-tert-butoxy-7a-(4-Bromo-benzyl)-3-(trichloromethyl)tetrahydro-1H-pyrrolo[1,2-c][1,3]oxazol-1-one (0.4 g) (Prep. 2) in 10 mL of MeOH was added 1 mL of dry HCl in ethyl ether, and the resulting solution was refluxed for 13 hrs. The MeOH was evaporated, and the residue dissolved in DCM and washed with aqueous $NaHCO_3$. The organic layer was dried over $MgSO_4$, filtered, and evaporated under reduced pressure to afford the above-titled compound (0.170 g). ¹H NMR (CDCl₃): 7.40 (2H,d), 7.05 (2H,d), 4.25 (1H, m), 3.65 (3H,s), 3.15 (1H,d), 2.85–3.0 (2H,m), 2.45–2.6 (2H,m), 1.85 (1H,dd).

Preparation 4

(6R,7aS)-7a-(4-bromobenzyl)-2-(3,5-dichlorophenyl)-6-hydroxytetrahydro-1H-pyrrolo[1,2-c]imidazole-1,3(2H)-dione

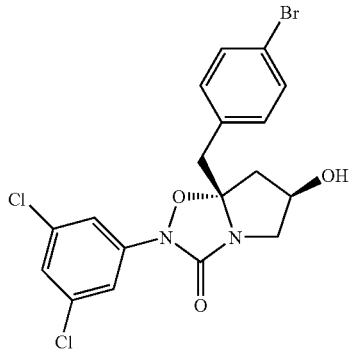

To a solution of methyl (4R)-2-(4-bromobenzyl)-4-hydroxy-L-prolinate (0.170 g) (Prep. 3) in 10 mL of DMF was added K₂CO₃ (0.15 g). The reaction mixture was cooled to 0° C., treated with 3,5-dichlorophenyl isocyanate (0.116 g), then allowed to warm to RT and stirred overnight. The insoluble material was removed by filtration, the DMF evaporated, and the residue dissolved in DCM. The organic layer was washed with water, dried over MgSO₄, and evaporated under reduced pressure. The resulting oily residue was purified over SiO₂ isolute column (10 g) (eluent: DCM/acetone-95/5) to afford the above-titled compound (0.100 g) as a white solid. ¹H NMR (CDCl₃): 7.45 (2H,d), 7.30 (1H,m), 7.10 (2H,d), 6.85 (2H,d), 4.75 (1H,m), 4.10 (1H,dd), 3.45 (1H,d), 3.40 (1H,dd), 3.25 (1H,d), 2.35 (1H,dd), 2.20 (1H,dd).

Preparation 5

(4R)-1-{[(3,5-dichlorophenyl)amino]carbonyl}-4-hydroxy-L-proline

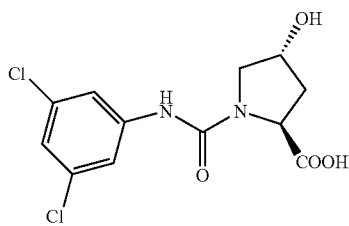

To a clear solution of L-trans-4-hydroxy-proline (10 g) (0.076 mol) and K₂CO₃ (15.7 g) (1.1 eq.) in 100 mL of water and 10 mL of THF, was added by portions 3,5-dichlorophenyl isocyanate (15.7 g) (1.1 eq.). The white suspension was stirred at RT overnight. The aqueous mixture was acidified with conc. HCl, then extracted with EtOAc. The organic extracts were combined, washed with water, dried over MgSO₄, filtered, and the solvent removed in vacuo to afford the titled compound (19 g) (yield 78.5%). ¹H NMR (DMSOd₆): 8.7 (1H,COOH), 7.65 (2H,d), 7.1 (1H,m), 5.2 (1H, NH), 4.4 (2H,m), 3.6 (1H,dd), 3.45 (1H,d), 2.1–2.25 (1H, m), 1.85–2.05 (1H,m).

Preparation 6

(6R,7aS)-2-(3,5-dichlorophenyl)-6-hydroxytetrahydro-1H-pyrrolo[1,2-c]imidazole-1,3(2H)-dione

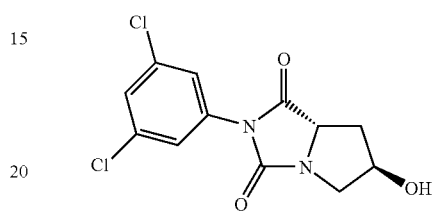

(4R)-1-{[(3,5-dichlorophenyl)amino]carbonyl}-4-hydroxy-L-proline (6.8 g) (0.021 mol) (Preparation 5) was combined with 35 mL of 1N HCl and refluxed for 11 hrs. The organic oil was separated from the reaction mixture and dissolved in EtOAc. The organic layer was washed with water, dried over MgSO₄, and evaporated under reduced pressure. The resulting residue was purified on a SiO₂ column (eluent: DCM/acetone-90/10) to afford the titled compound as a white solid (3.2 g). ¹H NMR (CDCl₃): 7.4 (2H,d), 7.35 (1H,m), 4.8 (1H,m), 4.60 (1H,dd), 3.98 (1H, dd), 3.35 (1H,d), 2.39 (1H,dd), 2.05 (1H,d,OH), 1.80–1.95 (1H,m).

Preparation 7

(6R,7aS)-2-(3,5-dichlorophenyl)-1,3-dioxohexahydro-1H-pyrrolo[1,2-c]imidazol-6-yl benzoate

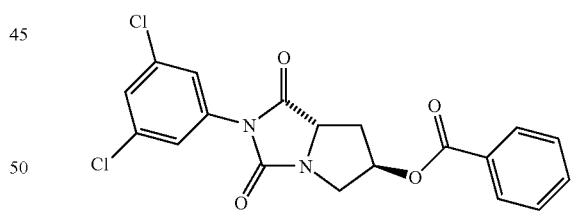

To a solution of (6R,7aS)-2-(3,5-dichlorophenyl)-6-hydroxytetrahydro-1H-pyrrolo[1,2-c]imidazole-1,3(2H)-dione (1.2 g) (4 mmol) (Preparation 6), dimethylaminopyridine (50 mg) (0.1 eq.) and benzoic acid (0.49 g) (1 eq.) in 10 mL of dry DCM at 0° C. was added DCC (0.9 g) (1 eq.) in a minimal volume of DCM. The reaction mixture was stirred to RT overnight. After filtering off the insoluble material, the reaction mixture is washed with a dilute NaHCO₃ aqueous solution, with dilute HCl solution, with water, dried over MgSO₄, and evaporated under reduced pressure to afford the titled compound as a viscous oil (1.54 g). ¹H NMR (CDCl₃): 8.05 (2H,d), 7.65 (1H,m), 7.5 (1H,d), 7.43 (2H,d), 7.38 (1H,m), 5.81 (1H,t), 4.62 (1H,dd), 4.23 (1H,dd), 3.56 (1H,d), 2.68 (1H,dd), 2.05–2.20 (1H,m).

Preparation 8 and 9

(6R,7aS)-7a-(4-cyanobenzyl)-2-(3,5-dichlorophenyl)-1,3-dioxohexahydro-1H-pyrrolo[1,2-c]imidazol-6-yl benzoate

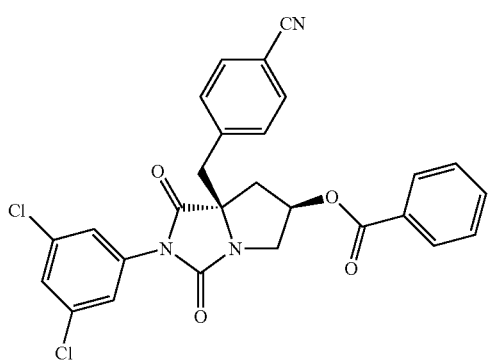

and (6R,7aR)-7a-(4-cyanobenzyl)-2-(3,5-dichlorophenyl)-1,3-dioxohexahydro-1H-pyrrolo[1,2-c]imidazol-6-yl benzoate

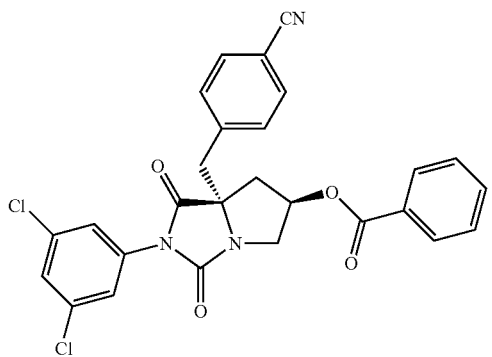

To a solution of (6R,7aS)-2-(3,5-dichlorophenyl)-1,3-dioxohexahydro-1H-pyrrolo[1,2-c]imidazol-6-yl benzoate (1.5 g) (3.7 mmol) (Preparation 7), and □-bromomethylbenzonitrile (0.72 g) (1 eq.) in 15 mL of dry DMSO was added in one portion finely grinded KOH (0.25 g) (1 eq.). The reaction mixture was stirred for 45 min at RT, then diluted with 150 mL of tButyl methyl ether. The organic phase was washed with water, dried over MgSO₄, filtered, and concentrated in vacuo. The residue afford the two diastereoisomers which were separated by column chromatography on silica (eluent: pet.ether-DCM 50/50).

Isomer 1 (6R,7aS)-7a-(4-cyanobenzyl)-2-(3,5-dichlorophenyl)-1,3-dioxohexahydro-1H-pyrrolo[1,2-c]imidazol-6-yl benzoate (0.52 g)

$^1$H NMR (CDCl$_3$): 8.05 (2H, d), 7.45–7.68 (5H, m), 7.34 (2H, d), 7.27 (1H, m), 6.93 (2H, d), 5.78 (1H, t), 4.47 (1H,dd), 3.64 (1H, dd), 3.58 (2H,bs), 2.45–2.67 (2H, m). M+(509)

Isomer 2 (6R,7aR)-7a-(4-cyanobenzyl)-2-(3,5-dichlorophenyl)-1,3-dioxohexahydro-1H-pyrrolo[1,2-c]imidazol-6-yl benzoate (0.37 g)

$^1$H NMR (CDCl$_3$): 7.82 (2H,d), 7.53–7.65 (3H,m), 7.35–7.45 (4H,m), 7.31 (1H,m), 6.75 (2H,d), 5.55 (1H,m), 4.36 (1H,dd), 3.32–3.42 (2H,d+dd), 3.06 (1H,d), 2.84 (1H, bd), 2.35 (1H,dd). M+(509)

Preparation 10

4-[(6R,7aS)-2-(3,5-dichlorophenyl) tetrahydro-6-hydroxy-1,3-dioxo-1H-pyrrolo[1,2-c]imidazol-7a (5H)-yl]-benzonitrile

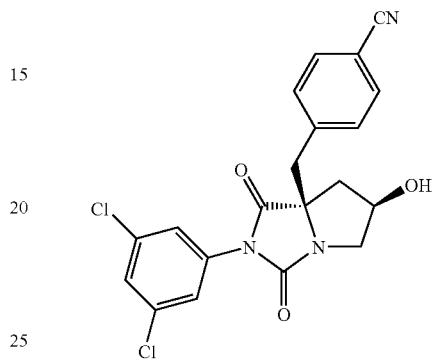

To a solution of (6R,7aS)-7a-(4-cyanobenzyl)-2-(3,5-dichlorophenyl)-1,3-dioxohexahydro-1H-pyrrolo[1,2-c]imidazol-6-yl benzoate (0.52 g) (1.02 mmol) (Preparation 8) in 1.5 mL of methanol and 4.5 mL of tBuOMe was added in one portion finely grinded KOH (0.057 g) (1 eq.). The reaction mixture was stirred for 5 min at RT, then quenched with 1 mL of 1N HCl, diluted with t-butyl methyl ether. The organic phase was washed with water, dried over MgSO₄, filtered, and concentrated in vacuo. The residue was purified by column chromatography on silica (eluent: pet.ether-DCM 50/50) to afford the titled compound (0.2 g)

$^1$H NMR (CDCl$_3$): 7.60 (2H,d), 7.30–7.35 (3H,m), 6.88 (2H,d), 4.82 (1H,m), 4.21 (1H,dd), 3.63 (1H,d), 3.45 (1H,d), 3.34 (1H,d), 2.29 (2H,m).

Preparation 11

(7aS)-7a-[(4-bromophenyl)methyl]-2-(3,5-dichlorophenyl)dihydro-1H-pyrrolo[1,2-c]imidazole-1,3,6 (2H,5H)-trione

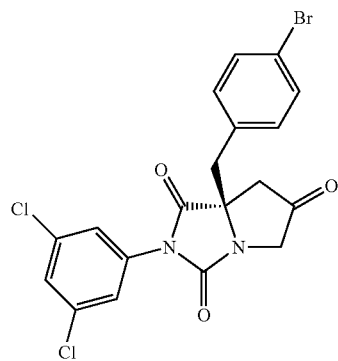

To a solution of (6R,7aS)-7a-(4-bromobenzyl)-2-(3,5-dichlorophenyl)-6-hydroxytetrahydro-1H-pyrrolo[1,2-c]

imidazole-1,3(2H)-dione (Preparation 4), (0.2 g, 0.42 mmol) in dichloromethane (5 mL) was added Dess-Martin periodane reagent (0.216 g, 0.504 mmol) in one lot at room temperature. The reaction mixture was stirred at room temperature for one hour and partitioned between dichloromethane (15 mL) and 1N NaOH (15 mL). The dichloromethane layer was washed with brine (2×20 mL), dried over sodium sulfate and concentrated to yield the title compound as a foamy solid (0.185 g). Retention time=3.84 min; column: YMC S5 Combiscreen ODS 4.6×50 mm (4 min. gradient); Solvent A=10% MeOH, 90% $H_2O$, 0.2% $H_3PO_4$; Solvent B=90% MeOH, 10% $H_2O$ and 0.2% $H_3PO_4$.

Preparation 12

4-[[(7aS)-2-(3,5-dichlorophenyl)-tetrahydro-1,3,6-trioxo-1H-pyrrolo[1,2-c]imidazol-7a(5H)-yl]methyl-benzonitrile

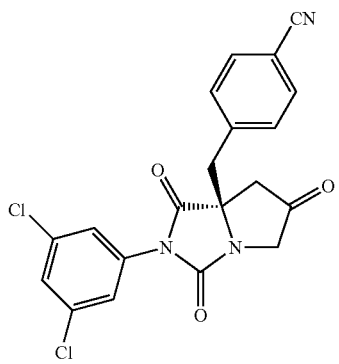

This compound was obtained using the protocol outlined for preparation 11 starting from 4-[(6R,7aS)-2-(3,5-dichlorophenyl)tetrahydro-6-hydroxy-1,3-dioxo-1H-pyrrolo[1,2-c]imidazol-7a(5H)-yl]-benzonitrile (Preparation 10), (0.2 g, 0.42 mmol). Yield: 0.193 g. $^1$H NMR (CDCl$_3$): 7.65 (2H, d), 7.25–7.35 (3H, m), 6.88 (2H, d), 4.25 (1H, d), 3.6 (1H, d), 3.35 (1H, d), 3.1 (1H, d), 2.85 (2H, q).

EXAMPLES

Example 1 and 2

(2R,5S,7a'S)-7a'-[(4-bromophenyl)-methyl]-2'-(3,5-dichlorophenyl)-5-methyldihydro-1'H,4H-spiro[1,3-oxazolidine-2,6'-pyrrolo[1,2-c]imidazole]-1',3',4(2'H)-trione

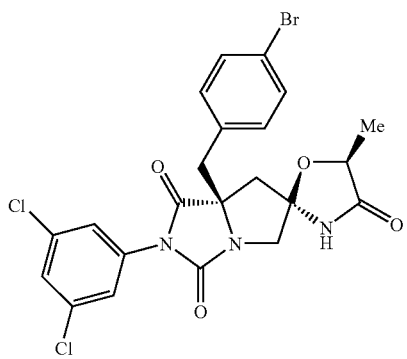

and (2R,5R,7a'S)-7a'-[(4-bromophenyl)-methyl]-2'-(3,5-dichlorophenyl)-5-methyldihydro-1'H,4H-spiro[1,3-oxazolidine-2,6'-pyrrolo[1,2-c]imidazole]-1',3',4(2'H)-trione To a solution of (7aS)-7a-[(4-bromophenyl)methyl]-2-(3,5-dichlorophenyl)dihydro-1H-pyrrolo[1,2-c]imidazole-1,3,6(2H,5H)-trione (preparation 11, 0.12 g, 0.26 mmol) and (S) lactamide (0.114 g, 1.3 mmol) in xylene (20 mL) was added para-toluenesulfonic acid (10 mgs) and the contents refluxed with the azeotropic removal of water for eighteen hours. The reaction mixture was cooled to room temperature, concentrated under reduced pressure and partitioned between dichloromethane (25 mL) and 1N sodium hydroxide (10 mL). The dichloromethane layer was dried over sodium sulfate, concentrated and purified by silica gel chromatography using hexane/ethyl acetate as the eluent.

Isomer 1: (2R,5S,7a'S)-7a'-[(4-bromophenyl)-methyl]-2'-(3,5-dichlorophenyl)-5-methyldihydro-1'H,4H-spiro[1,3-oxazolidine-2,6'-pyrrolo[1,2-c]imidazole]-1',3',4(2'H)-trione (35 mg).

$^1$H NMR (CDCl$_3$): 8.0 (1H, brs), 7.4 (2H, d), 7.3 (1H, m), 7.0 (2H, d), 6.8 (2H, s), 4.45 (1H, m), 4.0 (1H, d), 3.6 (1H, d), 3.35 (1H, d), 3.1 (1H, d), 1.4 (3H, d).

Isomer 2: (2R,5R,7a'S)-7a'-[(4-bromophenyl)-methyl]-2'-(3,5-dichlorophenyl)-5-methyldihydro-1'H,4H-spiro[1,3-oxazolidine-2,6'-pyrrolo[1,2-c]imidazole]-1',3',4(2'H)-trione (45 mg)

$^1$H NMR (CDCl$_3$): 7.8 (1H, brs), 7.4 (2H, d), 7.3 (1H, m), 7.1 (2H, d), 6.8 (2H, s), 4.35 (1H, m), 4.0 (1H, d), 3.15 (1H, d), 3.0 (1H, d), 2.9 (1H, d), 2.65 (1H, d), 2.25 (1H, d), 1.4 (3H, d).

The following examples were synthesized employing the protocol outlined for the preparation of Examples 1 and 2.

| Ex | Structure | Starting material | Coupling partner | Retention time[a] |
|---|---|---|---|---|
| 3 | 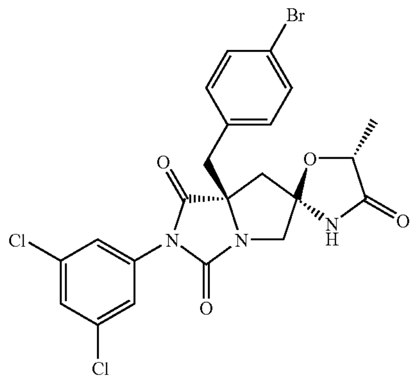 | | | |
| 4 | 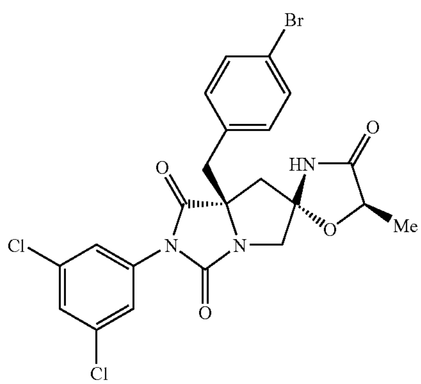 | | | |
| 5 | 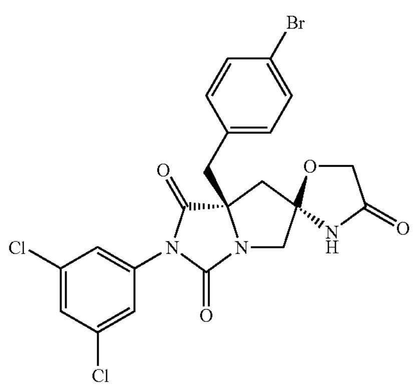 | | | 3.57 min |
| 6 | 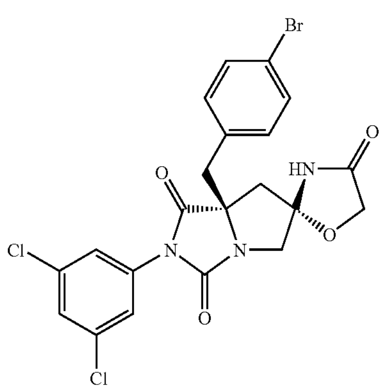 | | | 3.54 |

-continued

| Ex | Structure | Starting material | Coupling partner | Retention time[a] |
|---|---|---|---|---|
| 7 | 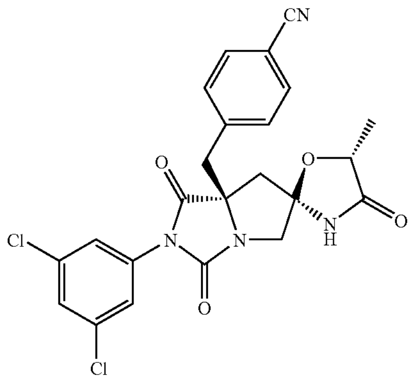 | | | 3.13 |
| 8 | 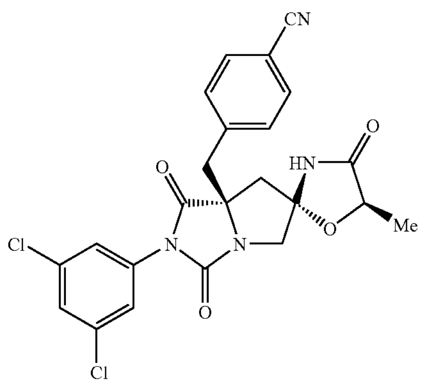 | | | 3.17 |

[a]Column conditions: YMC S5 Combiscreen ODS 4.6 × 50 nm (4 min. gradient); Solvent A = 10% MeOH, 90% H₂O, 0.1% TFA; Solvent B = 90% MeOH, 10% H₂O and 0.1% TFA.

Example 9

(2R,5R,7a'S)-2'-(3,5-dichlorophenyl)-7a'-[[4-(pyrimidin-4-yl)-phenyl)-methyl]-5-methyldihydro-1'H,4H-spiro[1,3-oxazolidine-2,6'-pyrrolo[1,2-c]imidazole]-1',3',4(2'H)-trione

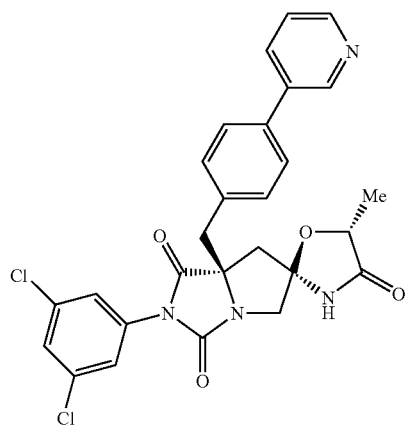

To a mixture of (2S,5S,7a'S)-7a'-[(4-bromophenyl)-methyl]-2'-(3,5-dichlorophenyl)-5-methyldihydro-1'H,4H-spiro[1,3-oxazolidine-2,6'-pyrrolo[1,2-c]imidazole]-1',3',4 (2'H)-trione (example 3, 0.02 g, 0.037 mmol) and 3-pyridylboronic acid (0.010 g, 0.08 mmol) in dimethoxyethane (2 mL) was sequentially added potassium carbonate (0.009 g, 0.069 mmol), and tetrakis (triphenylphosphine) palladium(0) (0.004 g). The reaction mixture was purged with nitrogen and heated at 80° C. for eighteen hours, cooled to room temperature and filtered over a thin pad of celite. The celite pad was washed with dichloromethane (10 mL) and the filtrate was subjected to preparative HPLC (YMC 20×100 mm; Solvent A=10% MeOH, 90% H2O, 0.1% trifluoroacetic acid; Solvent B=90% MeOH, 10% H₂O and 0.1% trifluoroacetic acid) to yield title compound as its trifluoroacetic acid salt. Yield: 2.8 mgs. Retention time=2.52 min. YMC ODS S5 C18 4.6×50 mm (4 min. gradient); Solvent A=10% MeOH, 90% H2O, 0.1% TFA; Solvent B=90% MeOH, 10% H₂O and 0.1% TFA.

Example 10 and 11 ethyl (4'S,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate

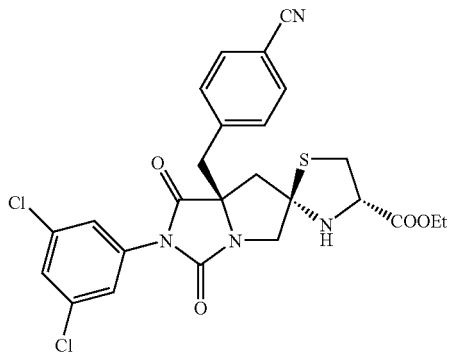

and ethyl (4'S,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate To a solution of 4-[[(7aS)-2-(3,5-dichlorophenyl)-tetrahydro-1,3,6-trioxo-1H-pyrrolo[1,2-c]imidazol-7a(5H)-yl]methyl-benzonitrile (preparation 12, 0.32 g, 0.77 mmol) and (D) Cysteine ethyl ester, hydrochloride (0.14 g, 0.77 mmol) in toluene (5 mL) was added ET₃N (1.21 ml, 1.54 mmol) then para-toluenesulfonic acid (10 mgs) and the contents refluxed with the azeotropic removal of water for five hours. The reaction mixture was cooled to room temperature, diluted with t-butyl methyl ether, washed with water, NaHCO₃ solution, water then dried over sodium sulfate, concentrated and purified by silica gel chromatography using dichloromethane/acetone as the eluent.

Isomer 1: (ethyl (4'S,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate):

yield: 0.016 g. ¹H NMR (CDCl₃): 7.6 (2H, d), 7.35 (2H, d), 7.3 (1H, m), 6.75 (2H, m), 4.2 (2H, q), 3.95 (1H, d), 3.9–3.7 (1H, m), 3.45–3.25 (2H, m), 3.1–2.85 (3H, m), 2.7–2.3 (2H, m+NH), 1.3 (3H,t).

Isomer 2: (ethyl (4'S,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate):

yield: 0.016 g. ¹H NMR (CDCl₃): 7.55 (2H, d), 7.4–7.2 (3H, m), 6.8 (2H, m), 4.4–4.2 (3H, m), 4.0 (1H, m), 3.7–3.0 (5H, m), 2.8 (NH), 2.65–2.35 (2H, dd), 1.3 (3H, t)

Example 12 and 13 ethyl (4'R,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate

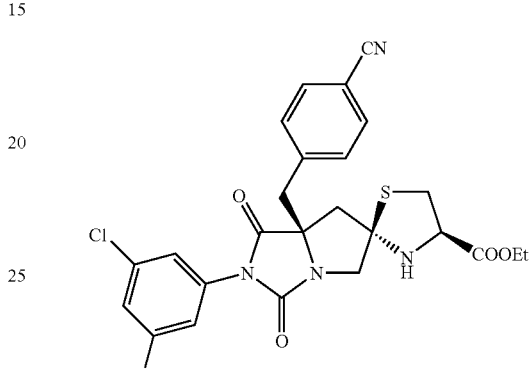

and ethyl (4'R,6S,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate

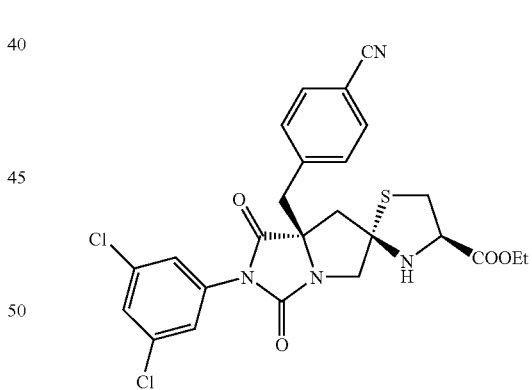

To a solution of 4-[[(7aS)-2-(3,5-dichlorophenyl)-tetrahydro-1,3,6-trioxo-1H-pyrrolo[1,2-c]imidazol-7a(5H)-yl]methyl-benzonitrile (preparation 12, 0.10 g, 0.24 mmol) and (L) Cysteine ethyl ester, hydrochloride (0.045 g, 0.24 mmol) in toluene (5 mL) was added ET₃N (0.06 ml, 0.48 mmol) then para-toluenesulfonic acid (10 mgs) and the contents refluxed with the azeotropic removal of water for five hours. The reaction mixture was cooled to room temperature, diluted with t-butyl methyl ether, washed with water, NaHCO₃ solution, water then dried over sodium sulfate, concentrated to give an oil (0.40 g), (0.10 g) of which was purified by silica gel chromatography using dichloromethane/acetone as the eluent.

Isomer 1: (ethyl (4'R,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate):

yield: 0.066 g. $^1$H NMR (CDCl$_3$): 7.65 (2H, d), 7.4 (2H, d), 7.3 (1H, m), 6.8 (2H, m), 4.25 (2H, q), 4.1 (1H, d), 3.9–3.75 (1H, m), 3.5–3.35 (2H, m), 3.3 (1H, d), 3.1–2.95 (2H, m), 2.75 (1H, d), 2.5 (NH, d), 2.15 (1H, d), 1.3 (3H, t).

Isomer 2: (ethyl (4'R,6S,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate):

yield: 0.025 g. $^1$H NMR (CDCl$_3$): 7.6 (2H, d), 7.35 (2H, d), 7.3 (1H, m), 6.85 (2H, m), 4.25 (2H, q), 4.1 (1H, d), 4.0–3.85 (1H, m), 3.55–3.45 (2H, m), 3.3 (2H, s), 3.159 (1H, dd), 3.0 (NH, d), 2.95 (1H, d), 2.55 (1H, d), 1.3 (3H, t).

Example 14

(±) ethyl (4'S,7aS)-3'-acetyl-7a-ethyl-2-methyl-1,3-dioxotetrahydro-1H-spiro[pyrrolo[1,2-c]imidazole-6,2'-[1,3]thiazolidine]-4'-carboxylate

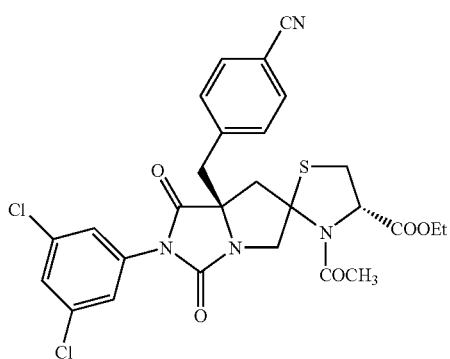

To a solution of ethyl (4'R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate (examples 12–13, crude mixture of isomers, 0.30 g, 0.58 mmol) and ET$_3$N (0.10 ml, 0.6 mmol)) in acetonitrile (3 mL) was added acetyl chloride (0.05 ml) and the contents stirred one night at RT. The reaction mixture was concentrated under reduced pressure and partitioned between dichloromethane (25 mL) and 1N Hydrochloric acid (10 mL). The dichloromethane layer was washed with 1N Sodium Bicarbonate, water then dried over sodium sulfate, concentrated and purified by silica gel chromatography using cyclohexane/ethyl acetate as the eluent, diluted with t-butyl methyl ether, washed with water, NaHCO$_3$ solution, water then dried over sodium sulfate, concentrated and purified by silica gel chromatography using dichloromethane/acetone as the eluent. yield: 0.016 g. $^1$H NMR (CDCl$_3$): 7.6 (2H, d), 7.35 (2H, d), 7.3 (1H, m), 6.8 (2H, m), 4.9 (1H, m), 4.75 (1H, d), 4.3 (2H, q), 4.05 (1H, d), 3.5–3.2 (5H, m), 2.65 (1H, d), 2.15 (3H, s), 1.3 (3H, t).

Example 15

(±) ethyl (4'S,7aS)-7a-(4-bromophenyl)-2-(3,5-dichlorophenyl)-1,3-dioxotetrahydro-1H-spiro[pyrrolo[1,2-c]imidazole-6,2'-[1,3]thiazolidine]-4'-carboxylate

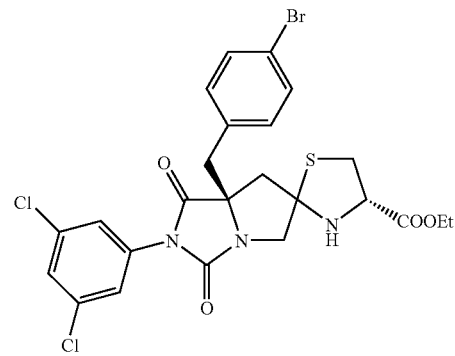

To a solution (7aS)-7a-[(4-bromophenyl)methyl]-2-(3,5-dichlorophenyl)dihydro-1H-pyrrolo[1,2-c]imidazole-1,3,6 (2H,5H)-trione (preparation 11, 1.0 g, 2.0 mmol) and (D) Cysteine ethyl ester, hydrochloride (0.40 g, 2.0 mmol) in toluene (10 mL) was added Et$_3$N (0.60 ml, 4.0 mmol) then para-toluenesulfonic acid (10 mg) and the contents refluxed with the azeotropic removal of water for seven hours. The reaction mixture was cooled to room temperature, diluted with t-butyl methyl ether, washed with water, NaHCO$_3$ solution, water then dried over sodium sulfate, concentrated and purified by silica gel chromatography using Ethyl acetate/Cyclohexane as the eluent. yield: 0.40 g. $^1$H NMR (CDCl$_3$): 7.4 (2H, d), 7.25 (1H, m), 7.1 (2H, d), 6.75 (2H, m), 4.15 (2H, q), 3.9 (1H, d), 3.82–3.76 (1H, m), 3.35 (1H, dd).

What is claimed is:

1. A compound of formula (I),

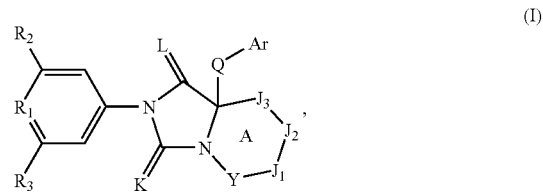

its stereoisomers, or a pharmaceutically-acceptable salt, hydrate, or prodrug thereof, in which:

K and L are independently O or S;

Q is a bond, —C(=O)— or branched or straight chain C$_{1-6}$alkylene optionally substituted with one to two R$_4$;

Ar is aryl or heteroaryl;

Y is a bond or —C(R$_{6a}$R$_{7a}$)—;

J$_1$ is —N(R$_5$)— or —C(R$_{6b}$R$_{7b}$)—;

J$_2$ is —N(R$_5$)— or —C(R$_{6c}$R$_{7c}$)—;

J$_3$ is N(R$_5$) or C(R$_{7d}$R$_{7d}$);

provided that only one of J$_1$, J$_2$ and J3 may be —N(R$_5$)—, so that ring A is a five-to six-membered cycloalkyl or heterocyclo ring having from 0 to 2 heteroatoms;

R$_1$ is N or C(R$_9$);

$R_2$ and $R_3$ are independently selected from hydrogen, halogen, nitro, cyano, alkyl, substituted alkyl, alkenyl, substituted alkenyl, —$SR_{12}$, —$OR_{12}$, —$NR_{12}R_{13}$, —$CO_2R_{12}$, —$C(=O)R_{12}$, —$C(=O)NR_{12}R_{13}$, aryl, heterocyclo, cycloalkyl, and heteroaryl;

$R_4$ is selected from OH, O($C_{1-6}$alkyl), halogen, cyano, $CF_3$, $OCF_3$, $NH_2$, NH($C_{1-6}$alkyl), and N($C_{1-6}$alkyl)$_2$;

$R_5$ is selected from hydrogen, alkyl, substituted alkyl, alkenyl, substituted alkenyl, —$NR_{14}R_{15}$, —$C(=O)R_{14}$, —$CO_2R_{14}$, —$C(=O)NR_{14}R_{15}$, —$S(O)_pR_{15a}$, —$SO_2NR_{14}R_{15}$, aryl, heterocyclo, cycloalkyl, and heteroaryl; or when $R_5$ is joined to atom $J_1$, $J_2$ or $J_3$, $R_5$ may be taken together with one of $R_{6a}$, $R_{6b}$, $R_{6c}$ or $R_{6d}$ attached to an adjacent atom of ring A to form a fused heterocyclo or heteroaryl ring;

at least one of $R_{6a}$ with $R_{7a}$, or $R_{6b}$ with $R_{7b}$, or $R_{6c}$ with $R_{7c}$ are taken together to form a spiro-cycloalkyl or spiro-heterocyclo ring; provided that the spiro-heterocyclo ring is not $C_{2-3}$ alkylenedioxy;

$R_{6a}$, $R_{6b}$, $R_{6c}$, $R_{6d}$, $R_{7a}$, $R_{7b}$, $R_{7c}$, and $R_{7d}$ which do not form a spiro-cycloalkyl or spiro-heterocyclo ring are independently selected from hydrogen, halogen, alkyl, substituted alkyl, alkenyl, substituted alkenyl, nitro, cyano, —$SR_{16}$, —$OR_{16}$, —$NR_{16}R_{17}$, —$C(=O)R_{16}$, —$CO_2R_{16}$, —$C(=O)NR_{16}R_{17}$, —$NR_{16}C(=O)R_{17}$, —$NR_{16}C(=O)OR_{17}$, —$S(O)_qR_{17a}$, —$NR_{16}SO_2R_{17a}$, —$SO_2NR_{16}R_{17}$, aryl, heterocyclo, cycloalkyl, and heteroaryl;

or $R_{6a}$, $R_{6b}$, $R_{6c}$, $R_{6d}$, $R_{7a}$, $R_{7b}$, $R_{7c}$, and $R_{7d}$ which do not form a spiro-cycloalkyl or spiro-heterocyclo ring and which are attached to the same carbon atom may be taken together to form a keto group;

or $R_{6a}$, $R_{6b}$, $R_{6c}$, $R_{6d}$, $R_{7a}$, $R_{7b}$, $R_{7c}$, and $R_{7d}$ which do not form a spiro-cycloalkyl or spiro-heterocyclo ring and which are attached to adjacent carbon atoms may be taken together to form a fused benzo, cycloalkyl, heterocyclo, or heteroaryl ring;

$R_9$ is selected from hydrogen, halogen, nitro, cyano, alkyl, substituted alkyl, alkenyl, substituted alkenyl, —$SR_{18}$, —$OR_{18}$, —$NR_{18}R_{19}$, —$CO_2R_{18}$, —$C(=O)R_{18}$, —$C(=O)NR_{18}R_{19}$, aryl, heterocyclo, cycloalkyl, and heteroaryl;

$R_{12}$, $R_{13}$, $R_{14}$, $R_{15}$, $R_{16}$, $R_{17}$, $R_{18}$, and $R_{19}$ (i) are selected independently of each from hydrogen, alkyl, substituted alkyl, cycloalkyl, aryl, heteroaryl, and heterocyclo; or (ii) any two of $R_{12}$, $R_{13}$, $R_{14}$, $R_{15}$, $R_{16}$, $R_{17}$, $R_{18}$, and $R_{19}$ when attached to the same nitrogen atom may be taken together to form a heteroaryl or heterocyclo ring, with the remainder of $R_{10}$, $R_{11}$, $R_{12}$, $R_{13}$, $R_{14}$, $R_{15}$, $R_{16}$, $R_{17}$, $R_{18}$, and $R_{19}$ being selected independently from hydrogen, alkyl, substituted alkyl, cycloalkyl, aryl, heteroaryl, and heterocyclo;

$R_{15a}$ and $R_{17a}$ are independently selected from alkyl, substituted alkyl, cycloalkyl, aryl, heteroaryl, and heterocyclo;

p is 1, 2, or 3; and q is 1, 2, or 3.

2. A compound according to claim 1, or a pharmaceutically-acceptable salt, hydrate, prodrug, or stereoisomer thereof, wherein:

K iand L are both O;

Q is a straight chain $C_{1-6}$alkylene;

Ar is phenyl optionally substituted one to three $R_{20}$;

$R_2$ and $R_3$ are selected from halogen, ($C_{1-6}$)alkyl, cyano, halo($C_{1-6}$)alkyl, halo($C_{1-6}$)alkoxy, nitro, phenyloxy, benzyloxy, and phenylthio;

$R_{20}$ at each occurrence is independently selected from halogen, $C_{1-6}$alkyl, hydroxy, ($C_{1-6}$)alkoxy, halo($C_{1-6}$)alkyl, halo($C_{1-6}$)alkoxy, cyano, nitro, —$CO_2H$, —$C(=O)H$, —$CO_2(C_{1-6})$alkyl, —$C(=O)$ ($C_{1-6}$)alkyl, —$C(=O)NH(CH_2)_rCO_2H$, —$C(=O)NH(CH_2)_rCO_2$ ($C_{1-6}$alkyl), and $S(O)_2(C_{1-6}$alkyl); or from phenyl, benzyl, phenyloxy, benzyloxy and heteroaryl in turn optionally substituted with one to two of halogen, $C_{1-6}$alkyl, hydroxy, ($C_{1-6}$)alkoxy, halo($C_{1-6}$)alkyl, halo ($C_{1-6}$)alkoxy, cyano, nitro, —$CO_2H$, —$C(=O)H$, —$CO_2(C_{1-6})$alkyl, and/or —$C(=O)$ ($C_{1-6}$)alkyl; or alternatively, two $R_{20}$ groups join together with each other to form a fused benzo ring; and r is 1, 2, 3, or 4.

3. A compound according to claim 2, or a pharmaceutically-acceptable salt, hydrate, prodrug, or stereoisomer thereof, wherein Q-Ar together form:

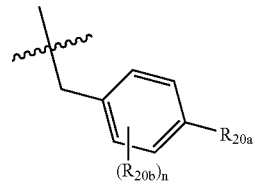

wherein $R_{20a}$ and $R_{20b}$ are independently selected from halogen, $C_{1-6}$alkyl, hydroxy, ($C_{1-6}$)alkoxy, halo($C_{1-6}$)alkyl, halo ($C_{1-6}$)alkoxy, cyano, nitro, —$CO_2H$, —$C(=O)H$, —$CO_2(C_{1-6})$alkyl, —$C(=O)$ ($C_{1-6}$)alkyl, —$C(=O)NH(CH_2)_rCO_2H$, —$C(=O)NH(CH_2)_rCO_2(C_{1-6}$alkyl), and $S(O)_2(C_{1-6}$alkyl); or from phenyl, benzyl, phenyloxy, benzyloxy and heteroaryl in turn optionally substituted with one to two of halogen, $C_{1-6}$alkyl, hydroxy, ($C_{1-6}$)alkoxy, halo($C_{1-6}$)alkyl, halo($C_{1-6}$)alkoxy, cyano, nitro, —$NH_2$, —$NH(C_{1-6}$alkyl), —$N(C_{1-6}$alkyl)$_2$, —$CO_2H$, —$C(=O)H$, —$CO_2(C_{1-6})$alkyl, and/or —$C(=O)(C_{1-6})$alkyl; or alternatively, two $R_{20b}$ groups join together with each other or one $R_{20b}$ joins together with $R_{20a}$ to form a fused benzo ring;

n is 0, 1, or 2; and r is 1, 2, 3, or 4.

4. A compound according to claim 1, or a pharmaceutically-acceptable salt, hydrate, prodrug, or stereoisomer thereof, wherein Y is a bond;

$J_3$ is —$CHR_{6b}$—;

$J_2$ is is —$C(R_{6c}R_{7c})$-wherein $R_{6c}$ with $R_7$, are taken together to form a spiro-cycloalkyl or spiro-heterocyclo ring;

$J_3$ is CH($R_{6d}$);

$R_{6b}$, and $R_{6d}$ are independently selected from a) hydrogen, halogen, and cyano;

b) —$SR_{16}$, —$OR_{16}$, —$NR_{16}R_{17}$, —$C(=O)R_{16}$, —$CO_2R_{16}$, —$C(=O)NR_{16}R_{17}$, —$NR_{16}C(=O)R_{17}$, —$NR_{16}C(=O)OR_{17}$, —$S(O)_qR_{17a}$, —$NR_{16}SO_2R_{17a}$, and —$SO_2NR_{16}R_{17}$; and c) $C_{1-6}$alkyl, phenyl, four to seven membered heterocyclo, $C_{3-7}$cycloalkyl, and five to six membered heteroaryl, each of which in turn is optionally substituted with one to two groups selected from $R_{22}$;

$R_{16}$ and $R_{17}$ are selected independently from hydrogen, $C_{1-6}$alkyl, phenyl, four to seven membered heterocyclo, $C_{3-7}$cycloalkyl, and five to six membered heteroaryl, each of which in turn is optionally substituted with one to two groups selected from $R_{23}$;

$R_{17a}$ is $C_{1-6}$alkyl, phenyl, four to seven membered heterocyclo, $C_{3-7}$cycloalkyl, five to six membered heteroaryl each of which is optionally substituted with one to two groups selected from $R_{23}$; and $R_{22}$ and $R_{23}$ are at each occurrence selected independently from halogen, cyano, $C_{1-6}$alkyl, hydroxy, trifluoromethyl, trifluoromethoxy, —O($C_{1-6}$alkyl), —C(=O)H, —C(=O)($C_{1-6}$alkyl), —CO$_2$H, —CO$_2$($C_{1-6}$alkyl), —C(=O)NH$_2$, —C(=O)NH$_2$, —C(=O)NH($C_{1-6}$alkyl), —C(=O)N($C_{1-6}$alkyl)$_2$, —NH$_2$, —NH($C_{1-6}$alkyl), —N($C_{1-6}$alkyl)$_2$, hydroxy($C_{1-6}$)alkyl, methoxy($C_{1-6}$)alkyl, ethoxy($C_{1-6}$)alkyl, amino($C_{1-6}$)alkyl, and halo($C_{1-6}$)alkyl.

5. The compound according to claim 1, or a pharmaceutically-acceptable salt, hydrate, prodrug, or stereoisomer thereof, in which
$R_1$ is $C(R_9)$; and
$R_2$ and $R_3$ are independently halogen.

6. A compound having the formula (Ia)

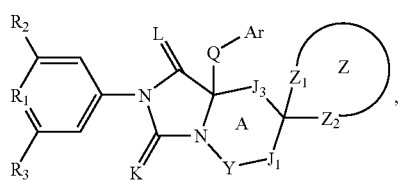

or a pharmaceutically-acceptable salt, hydrate, prodrug, or stereoisomer thereof, in which K and L are independently O or S;

Q is a bond, —C(=O)— or branched or straight chain $C_{1-6}$alkylene optionally substituted with one to two $R_4$;

Ar is aryl or heteroaryl;

Y is a bond or —C($R_{6a}R_{7a}$)—;

$J_1$ is —N($R_5$)— or —C($R_{6b}R_{7b}$)—;

$J_3$ is —N($R_5$)— or —C($R_{6d}R_{7d}$)—; provided, that only one of $J_1$ and $J_3$ may be —N($R_5$)—, so that ring A is a five-to-six membered cycloalkyl or heterocyclo ring having from 0 to 2 heteroatoms;

$Z_1$ and $Z_2$ are independently $NR_{25}$, S or O; so that Z forms a spiro heterocyclic ring provided that Z is not a $C_{2-3}$ alkylenedioxy ring and that only one of $Z_1$ and $Z_2$ may be $NR_{25}$;

$R_1$ is N or $C(R_9)$;

$R_2$ and $R_3$ are independently selected from hydrogen, halogen, nitro, cyano, alkyl, substituted alkyl, alkenyl, substituted alkenyl, —SR$_{12}$, —OR$_{12}$, —NR$_{12}$R$_{13}$, —CO$_2$R$_{12}$, —C(=O)R$_{12}$, —C(=O)NR$_{12}$R$_{13}$, aryl, heterocyclo, cycloalkyl, and heteroaryl;

$R_4$ is selected from OH, O($C_{1-6}$alkyl), halogen, cyano, CF$_3$, OCF$_3$, NH$_2$, NH($C_{1-6}$alkyl), and N($C_{1-6}$alkyl)$_2$;

$R_5$ is selected from hydrogen, alkyl, substituted alkyl, alkenyl, substituted alkenyl, —NR$_{14}$R$_{15}$, —C(=O)R$_{14}$, —CO$_2$R$_{14}$, —C(=O)NR$_{14}$R$_{15}$, —S(O)$_p$R$_{15a}$, —SO$_2$NR$_{14}$R$_{15}$, aryl, heterocyclo, cycloalkyl, and heteroaryl; or when $R_5$ is joined to atom $J_1$, $J_3$ or Y, $R_5$ may be taken together with one of $R_{6a}$, $R_{6b}$ or $R_{6d}$ attached to an adjacent atom of ring A to form a fused heterocyclo or heteroaryl ring;

$R_{6a}$, $R_{6b}$, $R_{6d}$, $R_{7a}$, $R_{7b}$, $R_{7b}$ and $R_{7d}$ are independently selected from hydrogen, halogen, alkyl, substituted alkyl, alkenyl, substituted alkenyl, nitro, cyano, —SR$_{16}$, —OR$_{16}$, —NR$_{16}$R$_{17}$, —C(=O)R$_{16}$, —CO$_2$R$_{16}$, —C(=O)NR$_{16}$R$_{17}$, —NR$_{16}$C(=O)R$_{17}$, —NR$_{16}$C(=O)OR$_{17}$, —S(O)$_q$R$_{17a}$, —NR$_{16}$SO$_2$R$_{17a}$, —SO$_2$NR$_{16}$R$_{17}$, aryl, heterocyclo, cycloalkyl, and heteroaryl;

$R_9$ is selected from hydrogen, halogen, nitro, cyano, alkyl, substituted alkyl, alkenyl, substituted alkenyl, —SR$_{18}$, —OR$_{18}$, —NR$_{18}$R$_{19}$, —CO$_2$R$_{18}$, —C(=O)R$_{18}$, —C(=O)NR$_{18}$R$_{19}$, aryl, heterocyclo, cycloalkyl, and heteroaryl;

$R_{12}$, $R_{13}$, $R_{14}$, $R_{15}$, $R_{16}$, $R_{17}$, $R_{18}$, and $R_{19}$ (i) are selected independently of each other from hydrogen, alkyl, substituted alkyl, cycloalkyl, aryl, heteroaryl, and heterocyclo; or (ii) any two of $R_{12}$, $R_{13}$, $R_{14}$, $R_{15}$, $R_{16}$, $R_{17}$, $R_{18}$, and $R_{19}$ when attached to the same nitrogen atom (as in NR$_{12}$R$_{13}$, NR$_{14}$R$_{15}$, NR$_{16}$R$_{17}$, or NR$_{18}$R$_{19}$) may be taken together to form a heteroaryl or heterocyclo ring, with the remainder of $R_{12}$, $R_{13}$, $R_{14}$, $R_{15}$, $R_{16}$, $R_{17}$, $R_{18}$, and $R_{19}$ being selected independently from hydrogen, alkyl, substituted alkyl, cycloalkyl, aryl, heteroaryl, and heterocyclo;

$R_{11a}$, $R_{15a}$, and $R_{17a}$ are independently selected from alkyl, substituted alkyl, cycloalkyl, aryl, heteroaryl, and heterocyclo;

$R_{25}$ is selected from hydrogen, alkyl, substituted alkyl, alkenyl, substituted alkenyl, —NR$_{26}$R$_{27}$, —C(=O)R$_{26}$, —CO$_2$R$_{26}$, —C(=O)NR$_{26}$R$_{27}$, —S(O)$_p$R$_{27}$, —SO$_2$NR$_{26}$R$_{27}$, aryl, heterocyclo, cycloalkyl, and heteroaryl;

$R_{26}$, and $R_{27}$ are selected independently of each other from hydrogen, alkyl, substituted alkyl, cycloalkyl, aryl, heteroaryl, and heterocyclo;

p is 0, 1, 2, or 3; and q is 1, 2, or 3.

7. A compound according to claim 6, or a pharmaceutically-acceptable salt, hydrate, prodrug, or stereoisomer thereof, in which Y is a bond; and Q-Ar together form:

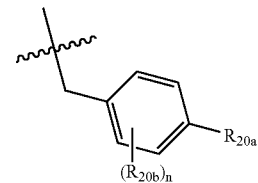

wherein $R_{20a}$ and $R_{20b}$ are independently selected from halogen, $C_{1-6}$alkyl, hydroxy, ($C_{1-6}$)alkoxy, halo($C_{1-6}$)alkyl, halo($C_{1-6}$)alkoxy, cyano, nitro, —CO$_2$H, —C(=O)H, —CO$_2$($C_{1-6}$)alkyl, —C(=O)($C_{1-6}$)alkyl, —C(=O)NH(CH$_2$)$_r$CO$_2$H, —C(=O)NH(CH$_2$)$_r$CO$_2$($C_{1-6}$alkyl), and S(O)$_2$($C_{1-6}$alkyl); or from phenyl, benzyl, phenyloxy, benzyloxy and heteroaryl in turn optionally substituted with one to two of halogen, $C_{1-6}$alkyl, hydroxy, ($C_{1-6}$)alkoxy, halo($C_{1-6}$)alkyl, halo($C_{1-6}$)alkoxy, cyano, nitro, —NH$_2$, —NH($C_{1-6}$alkyl), —N($C_{1-6}$alkyl)$_2$, —CO$_2$H, —C(=O)H, —CO$_2$($C_{1-6}$)alkyl, and/or —C(=O)($C_{1-6}$) alkyl; or alternatively, two $R_{20b}$ groups join together with each other or one $R_{20b}$ joins together with $R_{20a}$ to form a fused benzo ring;

n is 0, 1, or 2; and r is 1, 2, 3, or 4.

8. A compound according to claim 6, or a pharmaceutically-acceptable salt, hydrate, prodrug, or stereoisomer thereof, in which:
$R_2$ and $R_3$ are both halogen; and
$R_1$ is CH.

9. A compound according to claim 6, or a pharmaceutically-acceptable salt, hydrate, prodrug, or stereoisomer thereof, in which
Y is a bond;
$J_1$ is —$C(R_{6b}R_{7b})$—; and
$J_3$ is —$C(R_{6d}R_{7d})$—.

10. A compound according to claim 6, or a pharmaceutically-acceptable salt, hydrate, prodrug, or stereoisomer thereof, in which one of $Z_1$ or $Z_2$ is $NR_{25}$.

11. A compound of formula (Ib),

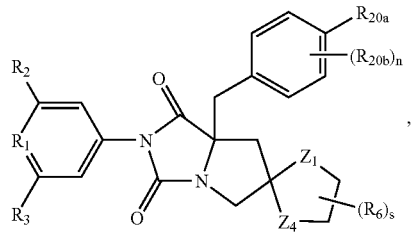

(Ib)

its stereoisomers, or a pharmaceutically-acceptable salt, hydrate, solvate, or prodrug thereof, in which:
one of $Z_1$ or $Z_2$ is $NR_{25}$ and the other of $Z_1$ or $Z_2$ is O or S;
$R_1$ is N or $C(R_9)$;
$R_2$ and $R_3$ are independently selected from halogen, $(C_{1-6})$ alkyl, cyano, halo$(C_{1-6})$alkyl, halo$(C_{1-6})$alkoxy, nitro, phenyloxy, benzyloxy, and phenylthio;
$R_6$ is selected from (a) halogen, nitro, and cyano; or from (b) —$SR_{16}$, —$OR_{16}$, —$NR_{16}R_{17}$, —$C(=O)R_{16}$, —$CO_2R_{16}$, —$C(=O)NR_{16}R_{17}$, —$NR_{16}C(=O)R_{17}$, —$NR_{16}C(=O)OR_{17}$, —$S(O)_qR_{17a}$, —$NR_{16}SO_2R_{17a}$, and —$SO_2NR_{16}R_{17}$; or from (c) alkyl, alkenyl, aryl, heterocyclo, cycloalkyl, and heteroaryl, in turn optionally substituted with one to two groups selected from $R_{22}$; and/or (d) two $R_6$ groups taken together form keto (=O), with the remainder of the $R_6$ groups selected from (a), (b), and (c);
$R_{16}$ and $R_{17}$ are selected independently of each other from hydrogen, $C_{1-6}$alkyl, phenyl, four to seven membered heterocyclo, $C_{3-7}$cycloalkyl, and five to six membered heteroaryl, each of which in turn is optionally substituted with one to two groups selected from $R_{23}$;
$R_{17a}$ is $C_{1-6}$alkyl, phenyl, four to seven membered heterocyclo, $C_{3-7}$cycloalkyl, five to six membered heteroaryl each of which is optionally substituted with one to two groups selected from $R_{23}$;
$R_{20a}$ and $R_{20b}$ are independently selected from halogen, $C_{1-6}$alkyl, hydroxy, $(C_{1-6})$alkoxy, halo$(C_{1-6})$alkyl, halo$(C_{1-6})$alkoxy, cyano, nitro, —$CO_2H$, —$C(=O)H$, —$CO_2(C_{1-6}$alkyl), —$C(=O)$ $(C_{1-6}$alkyl), —$C(=O)$ $NH(CH_2)_rCO_2H$, —$C(=O)NH(CH_2)_rCO_2(C_{1-6}$alkyl), and —$S(O)_2(C_{1-6}$alkyl); or from phenyl, benzyl, phenyloxy, benzyloxy and heteroaryl in turn optionally substituted with one to two of halogen, $C_{1-6}$alkyl, hydroxy, $(C_{1-6})$alkoxy, halo$(C_{1-6})$alkyl, halo$(C_{1-6})$ alkoxy, cyano, nitro, —$NH_2$, —$NH(C_{1-6}$alkyl), —$N(C_{1-6}$alkyl)$_2$, —$CO_2H$, —$C(=O)H$, —$CO_2(C_{1-6}$ alkyl, and/or —$C(=O)$ $(C_{1-6}$alkyl; or alternatively, two $R_{20b}$ groups join together with each other or one $R_{20b}$ joins together with $R_{20a}$ to form a fused benzo ring;
$R_{22}$, $R_{23}$ and $R_{24}$ are at each occurrence selected independently from halogen, cyano, nitro, $C_{1-6}$alkyl, hydroxy, trifluoromethyl, trifluoromethoxy, —$O(C_{1-6}$ alkyl), —$C(=O)H$, —$C(=O)(C_{1-6}$alkyl), —$CO_2H$, —$CO_2(C_{1-6}$alkyl), —$C(=O)NH_2$, —$C(=O)NH_2$, —$C(=O)NH(C_{1-6}$alkyl), —$C(=O)N(C_{1-6}$alkyl)$_2$, —$NH_2$, —$NH(C_{1-6}$alkyl), —$N(C_{1-6}$alkyl)$_2$, hydroxy $(C_{1-6})$alkyl, methoxy$(C_{1-6})$alkyl, ethoxy$(C_{1-6})$alkyl, amino$(C_{1-6})$alkyl, and halo$(C_{1-6})$alkyl;
$R_{25}$ is selected from hydrogen, alkyl, substituted alkyl, alkenyl, substituted alkenyl, —$NR_{26}R_{27}$, —$C(=O)$ $R_{26}$, —$CO_2R_{26}$, —$C(=O)NR_{26}R_{27}$, —$S(O)_pR_{27}$, —$SO_2NR_{26}R_{27}$, aryl, heterocyclo, cycloalkyl, and heteroaryl;
$R_{26}$ and $R_{27}$ are selected independently of each other from hydrogen, alkyl, substituted alkyl, cycloalkyl, aryl, heteroaryl, and heterocyclo
n, s and and p are independently 0, 1, or 2;
q is 1, 2, or 3; and
r is 0, 1, 2, 3 or 4.

12. A compound according to claim 11, or a pharmaceutically-acceptable salt, hydrate, prodrug, or stereoisomer thereof, in which $R_2$ and $R_3$ are independently halogen.

13. A compound according to claim 11, or a pharmaceutically-acceptable salt, hydrate, prodrug, or stereoisomer thereof, in which $R_{20a}$ is cyano, halogen, aryl, or heteroaryl.

14. A compound according to claim 11, or a pharmaceutically-acceptable salt, hydrate, prodrug, or stereoisomer thereof, in which
$R_1$ is CH;
$R_2$ and $R_3$ are independently halogen;
$R_6$ is hydrogen, $C_{1-6}$alkyl, substituted $C_{1-6}$alkyl, —$C(=O)R_{26}$ or $CO_2R_{26}$;
$R_{25}$ is hydrogen, $C_{1-6}$alkyl, substituted $C_{1-6}$alkyl, or —$C(=O)R_{26}$; and
n is 0.

15. A compound selected from the group consisting of,
(i) (2R,5S,7a'S)-7a'-[(4-bromophenyl)-methyl]-2'-(3,5-dichlorophenyl)-5-methyldihydro-1'H,4H-spiro[1,3-oxazolidine-2,6'-pyrrolo[1,2-c]imidazole]-1',3',4(2'H)-trione;
(2R,5R,7a'S)-7a'-[(4-bromophenyl)-methyl]-2'-(3,5-dichlorophenyl)-5-methyldihydro-1'H,4H-spiro[1,3-oxazolidine-2,6'-pyrrolo[1,2-c]imidazole]-1',3',4(2'H)-trione;
(2R,5R,7a'S)-7a'-[(4-Bromophenyl)methyl]-2'-(3,5-dichlorophenyl)dihydro-5-methylspiro[oxazolidine-2,6'(5'H)-[1H]pyrrolo[1,2-c]imidazole]-1',3',4(2'H)-trione;
(2S,5R,7a'S)-7a'-[(4-Bromophenyl)methyl]-2'-(3,5-dichlorophenyl)dihydro-5-methylspiro[oxazolidine-2,6'(5'H)-[1H]pyrrolo [1,2-c]imidazole]-1',3',4(2'H)-trione;
(2R,7a'S)-7a'-[(4-Bromophenyl)methyl]-2'-(3,5-dichlorophenyl)dihydrospiro[oxazolidine-2,6'(5'H)-[1H]pyrrolo[1,2-c]imidazole]-1',3',4(2'H)-trione;
(2S,7a'S)-7a'-[(4-Bromophenyl)methyl]-2'-(3,5-dichlorophenyl)dihydrospiro[oxazolidine-2,6'(5'H)-[1H] pyrrolo[1,2-c]imidazole]-1',3',4(2'H)-trione;
4-[[(2R,5R,7a'S)-2'-(3,5-Dichlorophenyl)dihydro-5-methyl-1',3',4-trioxospiro[oxazolidine-2,6'(5'H)-[1H]pyrrolo[1,2-c]imidazol]-7a'(7'H)-yl]methyl] benzonitrile;

4-[[(2S,5R,7a'S)-2'-(3,5-Dichlorophenyl)dihydro-5-methyl-1',3',4-trioxospiro[oxazolidine-2,6'(5'H)-[1H]pyrrolo[1,2-c]imidazol]-7'a(7'H)-yl]methyl]-benzonitrile;

(2R,5R,7a'S)-2'-(3,5-dichlorophenyl)-7a'-[[4-(pyrimidin-4-yl)-phenyl]-methyl]-5-methyldihydro-1'H,4H-spiro[1,3-oxazolidine-2,6'-pyrrolo[1,2-c]imidazole]-1',3',4(2'H)-trione;

ethyl (4'S,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate;

ethyl (4'S,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate;

ethyl (4'R,6R,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate;

ethyl (4'R,6S,7aS)-7a-(4-cyanophenyl)-2-(3,5-dichlorophenyl)-1,3-dioxotetrahydro-1H-spiro[pyrrolo[1,2-c]imidazole-6,2'-[1,3]thiazolidine]-4'-carboxylate;

(±) ethyl (4'S,7aS)-3'-acetyl-7a-ethyl-2-methyl-1,3-dioxotetrahydro-1H-spiro[pyrrolo[1,2-c]imidazole-6,2'-[1,3]thiazolidine]-4'-carboxylate; or (±) ethyl (4'S,7aS)-7a-(4-bromophenyl)-2-(3,5-dichlorophenyl)-1,3-dioxotetrahydro-1H-spiro[pyrrolo[1,2-c]imidazole-6,2'-[1,3]thiazolidine]-4'-carboxylate; or (ii) a pharmaceutically-acceptable salt, hydrate, prodrug, or stereoisomer of (i).

16. A pharmaceutical composition comprising at least one compound according to claim 1 and a pharmaceutically acceptable carrier or diluent.

17. A pharmaceutical composition comprising at least one compound according to claim 15 and a pharmaceutically acceptable carrier or diluent.

18. A method of inhibiting an LFA-1/ICAM-associated condition in a mammal to treat a disease selected from the group consisting of acute or chronic transplant rejection, rheumatoid arthritis, osteoarthritis, diabetes, asthma, inflammatory bowel disease, psoriasis, and chronic obstructive pulmonary disease comprising administering to the mammal a therapeutically-effective amount of a compound according to claim 1.

* * * * *